（12）United States Patent
Lucas et al.

(10) Patent No.: US 10,957,433 B2
(45) Date of Patent: Mar. 23, 2021

(54) CLINICAL CONCEPT IDENTIFICATION, EXTRACTION, AND PREDICTION SYSTEM AND RELATED METHODS

(71) Applicant: Tempus Labs, Chicago, IL (US)

(72) Inventors: Michael Lucas, Chicago, IL (US); Jonathan Ozeran, Chicago, IL (US); Jason Taylor, Chicago, IL (US); Louis Fernandes, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 16/702,510

(22) Filed: Dec. 3, 2019

(65) Prior Publication Data

US 2020/0176098 A1    Jun. 4, 2020

Related U.S. Application Data

(60) Provisional application No. 62/774,854, filed on Dec. 3, 2018.

(51) Int. Cl.
| | |
|---|---|
| *G16H 15/00* | (2018.01) |
| *G06F 40/30* | (2020.01) |
| *G16H 10/60* | (2018.01) |
| *G16H 70/00* | (2018.01) |
| *G06F 40/295* | (2020.01) |

(52) U.S. Cl.
CPC ........... *G16H 15/00* (2018.01); *G06F 40/295* (2020.01); *G06F 40/30* (2020.01); *G16H 10/60* (2018.01); *G16H 70/00* (2018.01)

(58) Field of Classification Search
None
See application file for complete search history.

(56) References Cited

U.S. PATENT DOCUMENTS

| 6,804,656 | B1 | 10/2004 | Rosenfeld |
| 9,031,926 | B2 | 5/2015 | Milward et al. |
| 9,208,217 | B2 | 12/2015 | Milward et al. |
| 2002/0173702 | A1 | 11/2002 | Lebel |
| 2004/0122790 | A1 | 6/2004 | Walker |
| 2007/0005621 | A1* | 1/2007 | Lesh ...................... G16H 15/00 |

(Continued)

OTHER PUBLICATIONS

"Algorithm Implementation/Strings/Levenshtein distance," Wikibooks, last edited on Jan. 5, 2019, 39 pages. Retrieved from Internet. URL: https://en.wikibooks.org/wiki/Algorithm_Implementation/Strings/Levenshtein_distance#Python.

(Continued)

*Primary Examiner* — Aryan E Weisenfeld
*Assistant Examiner* — Karen A Hranek
(74) *Attorney, Agent, or Firm* — Quarles & Brady LLP

(57) ABSTRACT

A method includes the steps of determining a first concept from a text of a medical record from an electronic health record system, the first concept relating to a patient, identifying a match to the first concept in a first list of concepts, wherein the first list of concepts is not a predetermined authority, referencing the first concept with an entity in a database of related concepts, identifying a match to a second concept in a second list of concepts, the second list of concepts not directly linked to the first list of concepts except by a relationship to the entity, wherein the second list of concepts is the predetermined authority, and providing the second concept as an identifier of the patient's medical record.

26 Claims, 9 Drawing Sheets

(56) References Cited

U.S. PATENT DOCUMENTS

| | | | |
|---|---|---|---|
| 2008/0162393 | A1 | 7/2008 | Illiff |
| 2011/0288877 | A1* | 11/2011 | Ofek ............... G16H 10/60 705/2 |
| 2012/0110016 | A1* | 5/2012 | Phillips ............ G06Q 50/22 707/780 |
| 2012/0265544 | A1 | 10/2012 | Hwang |
| 2013/0096947 | A1* | 4/2013 | Shah ............... G06Q 50/24 705/3 |
| 2013/0246049 | A1* | 9/2013 | Mirhaji ........... G06F 16/3344 704/9 |
| 2014/0122117 | A1* | 5/2014 | Masarie, Jr. ...... G16H 10/60 705/3 |
| 2014/0244625 | A1 | 8/2014 | Seghezzi |
| 2014/0249761 | A1 | 9/2014 | Carroll |
| 2014/0278461 | A1* | 9/2014 | Artz ............ G06Q 10/06314 705/2 |
| 2014/0280353 | A1* | 9/2014 | Delaney ............ G16H 10/60 707/794 |
| 2015/0006558 | A1* | 1/2015 | Leighton .......... G06F 16/243 707/756 |
| 2015/0106125 | A1* | 4/2015 | Farooq ............ G06F 40/30 705/3 |
| 2015/0178386 | A1* | 6/2015 | Oberkampf ........ G06F 19/32 707/749 |
| 2015/0213194 | A1 | 7/2015 | Wolf |
| 2015/0331909 | A1 | 11/2015 | Sundquist |
| 2017/0046425 | A1* | 2/2017 | Tonkin ............ G06F 16/367 |
| 2017/0177597 | A1 | 6/2017 | Asimenos |
| 2017/0237805 | A1 | 8/2017 | Worley |
| 2018/0046764 | A1* | 2/2018 | Katwala ........... G16H 15/00 |
| 2018/0060523 | A1* | 3/2018 | Farh .............. G06N 5/04 |
| 2018/0121618 | A1* | 5/2018 | Smith ............. G06F 40/242 |
| 2018/0373844 | A1* | 12/2018 | Ferrandez-Escamez ......... G06F 40/284 |
| 2019/0057774 | A1* | 2/2019 | Velez ............. G16H 10/40 |
| 2019/0206524 | A1* | 7/2019 | Baldwin ........... G16H 20/00 |

OTHER PUBLICATIONS

"Amazon Textract—Easily extract text and data from virtually any document," Amazon, Nov. 28, 2018, 6 pages. Retrieved from Internet. URL: https://aws.amazon.com/textract/.

"CliNER," Text Machine Lab 2014, Nov. 10, 2017, 2 pages. Retrieved from Internet. URL: http://text-machine.cs.uml.edu/cliner/.

"Clinithink CLiX CNLP (Harness unstructured data to drive value across the healthcare continuum)," Clinithink Limited, 2015, 1 page. Retrieved from Internet. URL: http://clinithink.com/wp-content/uploads//2015/01/Clinithink-CLiX-CNLP-Sell-Sheet-US.pdf.

"Evernote Scannable on the App Store," Jun. 18, 2018, 3 pages. Retrieved from Internet. URL: https://itunes.apple.com/us/app/evernote-scannable/id883338188?mt=8.

"I2E: The world's leading Text Mining platform," 2019 Linguamatics, Aug. 14, 2018, 5 pages. Retrieved from Internet. URL: https://www.linguamatics.com/products-services/about-i2e.

"PHP: levenshtein—Manual," latest comment dated in 2014, 32 pages. Retrieved from Internet. URL: http://www.php.net/levenshtein.

"Talk:Algorithm implementation/Strings/Levenshtein distance," Wikibooks, last edited on Nov. 2, 2016, 2 pages. Retrieved from Internet. URL: https://en.wikibooks.org/wiki/Talk:Algorithm_Implementation/Strings/Levenshtein_distance#Bug_in_vectorized_(5th)_version.

"Why cTAKES? See the animation below for a sampling of cTAKES capabilities," The Apache Software Foundation, Apr. 25, 2017, 1 page. Retrieved from Internet. URL: http://ctakes.apache.org/whycTAKES.html.

Aronson, Alan "MetaMap—A Tool for Recognizing UMLS Concepts in Text," Jan. 11, 2019, 2 pages. Retrieved from Internet. URL: https://metamap.nlm.nih.gov/.

Balatero, David (dbalatero/levenshtein-ffi) "Fast string edit distance computation, using the Damerau-Levenshtein algorithm," GitHub, Inc., latest comment dated on Aug. 10, 2014, 2 pages. Retrieved from Internet. URL: https://github.com/dbalatero/levenshtein-ffi.

Chen, Huizhong et al. "Robust Text Detection in Natural Images With Edge-Enhanced Maximally Stable Extremal Regions," 2011 18th IEEE International Conference on Image Processing, Sep. 11-14, 2011, 4 pages.

Choi, Edward et al. "Doctor AI: Predicting Clinical Events via Recurrent Neural Networks," Proceedings of Machine Learning for Healthcare 2016, JMLR W&C Track vol. 56, 2016, pp. 1-18.

Choi, Edward et al. "Coarse-to-Fine Question Answering for Long Documents," Proceedings of the 55th Annual Meeting of the Association for Computational Linguistics, Vancouver, Canada, Jul. 30-Aug. 4, 2017, pp. 209-220.

Collobert, Ronan et al. "Natural Language Processing (Almost) from Scratch," Journal of Machine Learning Research 12, (2011) pp. 2493-2537.

Conneau, Alexis et al. "Very Deep Convolutional Networks for Text Classification," arXiv:1606.01781 [cs.CL], Jan. 27, 2017, 10 pages.

Das, Rajarshi et al. "Chains of Reasoning over Entities, Relations, and Text using Recurrent Neural Networks," Proceedings of the 15th Conference of the European Chapter of the Association for Computational Linguistics: vol. 1, Valencia, Spain, Apr. 3-7, 2017, pp. 132-141.

De Bruijn, Berry et al. "Machine-learned solutions for three stages of clinical information extraction: the state of the art at i2b2 2010," 18 J. Am. Med. Inform. Assoc. 2011, May 12, 2011, pp. 557-562.

Dozat, Timothy et al. "Deep Biaffine Attention for Neural Dependency Parsing," Published as a conference paper at ICLR 2017, arXiv:1611.01734 [cs.CL], Mar. 10, 2017, pp. 1-8.

Genthial, Guillaume "Sequence Tagging with Tensorflow (bi-LSTM + CRF with character embeddings for NER and POS)," Guillaume Genthial blog, Apr. 5, 2017, 23 pages.

He, Dafang et al. "Multi-scale Multi-task FCN for Semantic Page Segmentation and Table Detection," IEEE, 2017 14th IAPR International Conference on Document Analysis and Recognition, Nov. 9-15, 2017, pp. 254-261.

He, Luheng et al. "Deep Semantic Role Labeling: WhatWorks and What's Next" Proceedings of the 55th Annual Meeting of the Association for Computational Linguistics, Vancouver, Canada, Jul. 30-Aug. 4, 2017, pp. 473-483.

Kavasidis, I. et al. "A Saliency-based Convolutional Neural Network for Table and Chart Detection in Digitized Documents," Submitted to IEEE Transactions on Multimedia, Apr. 17, 2018, pp. 1-13.

Kim, Youngjun et al. "A Study of Concept Extraction Across Different Types of Clinical Notes," AMIA Annu Symp Proc. 2015; Nov. 5, 2015, pp. 737-746.

Lafferty, John et al. "Conditional Random Fields: Probabilistic Models for Segmenting and Labeling Sequence Data," Proceedings of the 18th International Conference on Machine Learning 2001 (ICML 2001), Jun. 28, 2001, pp. 282-289.

Lample, Guillaume et al. "Neural Architectures for Named Entity Recognition," Association for Computational Linguistics, Proceedings of NAACL-HLT 2016, San Diego, California, Jun. 12-17, 2016, pp. 260-270.

Lang, Francois-Michel et al. "Increasing UMLS Coverage and Reducing Ambiguity via Automated Creation of Synonymous Terms: First Steps toward Filling UMLS Synonymy Gaps," Semantic Scholar, 2017, pp. 1-26.

Laserson, Jonathan et al. "TextRay: Mining Clinical Reports to Gain a Broad Understanding of Chest X-rays," arXiv:1806.02121 [cs.CV], Jun. 6, 2018, 13 pages.

Lee, Kenton et al. "End-to-end Neural Coreference Resolution," arXiv:1707.07045 [cs.CL], Dec. 15, 2017, 10 pages.

Lei, Tao et al. "Rationalizing Neural Predictions," arXiv:1606.04155 [cs.CL], Nov. 2, 2016, 11 pages.

Ling, Yuan et al. "Learning to Diagnose: Assimilating Clinical Narratives using Deep Reinforcement Learning," Proceedings of the the 8th International Joint Conference on Natural Language Processing, Taipei, Taiwan, Nov. 27-Dec. 1, 2017, pp. 895-905.

(56) References Cited

OTHER PUBLICATIONS

Lipton, Zachary et al. "Learning to Diagnose With LSTM Recurrent Neural Networks," ICLR 2016, arXiv:1511.03677 [cs.LG], pp. 1-18.
Ma, Xuezhe et al. "End-to-end Sequence Labeling via Bi-directional LSTM-CNNs-CRF," arXiv:1603.01354v5 [cs.LG], May 29, 2016, 12 pages.
Mackenzie, Andrei (andrei-m/levenshtein.js) "Levenshtein distance between two given strings implemented in JavaScript and usable as a Node.js module," GitHub, Inc., latest comment dated on Feb. 2, 2018, 9 pages. Retrieved from Internet. URL: https://gist.github.com/andrei-m/982927.
Mihalcea, Rada et al. "Part IV Graph-Based Natural Language Processing" excerpted from a book "Graph-Based Natural Language Processing and Information Retrieval," Cambridge University Press, First published 2011 (Reprinted 2012), 63 pages.
Mysore, Sheshera S. "Segmentation of Non-text Objects with Connected Operators" Msheshera, May 21, 2017, 2 pages. Retrieved from Internet. URL: http://msheshera.github.io/non-text-segment-connected-operators.html.
Narasimhan, Karthik et al. "Improving Information Extraction by Acquiring External Evidence with Reinforcement Learning," arXiv:1603.07954v3 [cs.CL], Sep. 27, 2016, 12 pages.
Neelakantan, Arvind et al. "Learning Dictionaries for Named Entity Recognition using Minimal Supervision," Proceedings of the 14th Conference of the European Chapter of the Association for Computational Linguistics, Gothenburg, Sweden, Apr. 26-30, 2014, pp. 452-461.
Peters, Matthew. E. et al. "Semi-supervised sequence tagging with bidirectional language models," arXiv:1705.00108v1 [cs.CL], Apr. 29, 2017, 10 pages.
Prakash, Aaditya et al. "Condensed Memory Networks for Clinical Diagnostic Inferencing," arXiv:1612.01848v2 [cs.CL], Jan. 3, 2017, 8 pages.
Sager, Naomi et al. "Natural Language Processing and the Representation of Clinical Data," Journal of the American Medical Informatics Association, vol. 1, No. 2, Mar./Apr. 1994, pp. 142-160.
Sambyal, Nitigya et al. "Automatic Text Extraction and Character Segmentation Using Maximally Stable Extremal Regions," arXiv:1608.03374 [cs.CV], Aug. 11, 2016, 6 pages.
Tsou, Ching-Huei et al. "Watson for Patient Record Analytics (aka Watson EMRA)," IBM Research, Aug. 2017, 5 pages. Retrieved from Internet. URL: https://researcher.watson.ibm.com/researcher/view_group.php?id=7664.
Wu, Yonghui et al. "A Study of Neural Word Ernbeddings for Named Entity Recognition in Clinical Text," AMIA Annual Symp. Proc. 2015; Published online Nov. 5, 2015, pp. 1326-1333.
Zhang, Yuan et al. "Aspect-augmented Adversarial Networks for Domain Adaptation" sentiarXiv:1701.00188v2 [cs. CL], Sep. 25, 2017, 14 pages.
Zeng, et al., "Extracting principal diagnosis, co-morbidity and smoking status for asthma research: evaluation of a natural language processing system", BMC Medical Informatics and Decision Making 2006, 6:30, retrieved from the internet at: https://bmcmedinformciecismak.biomedcentral.com/articles/10.1186/1472-6947-6-30 on Dec. 3, 2019, 9 pages.
Savova, et al., "Mayo clinical Text Analysis and Knowledge Extraction System (cTAKES): architecture, component evaluation and applications", J Am Med Inform Assoc 2010;17: 507 - 513., retrieved from the internet at: https://academic.oup.com/jamia/article/17/5/507/830823, on Dec. 3, 2019, 7 pages.
International Searching Authority. International Search Report and Written Opinion for application PCT/US2020/047704. dated Nov. 20, 2020.
Dnanexus. Working with UK Biobank: A Research Guide. Accessed online on Dec. 31, 2020. Available at https://web.archive.org/save/https://dna-nexus-prod-s3-assets-51tcpaqcp0pd.s3.amazonaws.com/images/files/DNAnexus_WhitePaper_Working-with-UKB-Data_2.pdf.
CARIS Life Sciences. Code: Comprehensive Oncology Data Explorer. Slideshow May 2017. Accessed on Dec. 16, 2020 at https://www.karmanos.org/Uploads/Public/Documents/Karmanos/CODE%20slides_5.2017.pptx%20.

* cited by examiner

| Field | Value |
|---|---|
| Text | "The patient was given Tylenol 50mg at 10:35am." |
| Medication | Tylenol |
| Active Ingredient | acetaminophen |
| Dosage | 50mg |
| Date Administered | 01/01/2001 10:35:01 am CST |
| Document | Progress Note 01_01_1.pdf |
| Page | 3 |
| UMLS CUI | C1234567 |
| UMLS_AUI | RXNORM#12345 |

FIG. 2

Text

The Patient Was Given Tylenol 50mg at 11:35 am.

The Patient Underwent a lumpectomy to remove an area of Ductal Carcinoma in Situ.

After the patient's procedure, they will receive brachytherapy.

Score/Weight

Sentence 1: 95% medication = Tylenol 50mg

Sentence 2: 97% procedure = lumpectomy

Sentence 3: 85% procedure = brachytherapy

FIG. 4

| The | patient | was | given | Tylenol | 50mg | at | 11:35 am |
|---|---|---|---|---|---|---|---|
| B = 90% | B = 5% | B = 0% | B = 0% | B = 60% | B = 5% | B = 0% | B = 0% |
| I = 10% | I = 20% | I = 0% | I = 0% | I = 0% | I = 60% | I = 0% | I = 0% |
| O = 0% | O = 75% | O = 100% | O = 100% | O = 40% | O = 35% | O = 100% | O = 100% |

| The | Patient | | | Tylenol | 50mg | | 11:35 am |
|---|---|---|---|---|---|---|---|
| B | I | | | B | I | | O |

CLINICAL CONCEPT IDENTIFICATION, EXTRACTION, AND PREDICTION SYSTEM AND RELATED METHODS

CROSS-REFERENCE TO RELATED APPLICATIONS

This application claims the benefit of priority to U.S. provisional application 62/774,854, filed Dec. 3, 2018, the contents of which are incorporated herein by reference in their entirety.

BACKGROUND OF THE DISCLOSURE

1. Field of the Invention

The field of the disclosure is a system and method that incorporates machine learning to identify, extract, and predict clinical concepts from electronic health and medical records.

2. Description of the Related Art

Conventional electronic health record (EHR) and electronic medical record (EMR) systems lack the ability to capture and store critical components of a patient's history, demographics, diagnosis, treatments, outcomes, genetic markers, etc., because they focus on billing operations and compliance with regulatory requirements that mandate collection of a certain subset of attributes. This problem may be exacerbated by the fact that parts of a patient's record which may include rich and meaningful data (e.g., diagnoses and treatments captured in progress or follow-up notes, flow sheets, pathology reports, radiology reports, etc.) remain isolated, unstructured, and inaccessible within the patient's record as uncatalogued, unstructured documents stored in accompanying systems. Conventional methods for identifying and structuring this data are reliant on human analysts reviewing documents and entering the data into a record system manually. A majority of the conventional systems in use lack the ability to mine and/or uncover this information, leading to gaps in data accessibility and inhibiting a physician's ability to provide optimal care (i.e., precision medicine).

Conventional systems for identifying and structuring data are lacking in quality and robustness for preprocessing or extracting meaningful records from multiple sources of health or medical record data. For example, physicians and clinical staff may record handwritten notes in shorthand in the margins of a document which is then scanned into an EHR or EMR system. Such entries to the EHR or EMR are difficult to account for without an intervening analyst to interpret the record. Furthermore, locating relevant data throughout a document relies on isolating and identifying information that provides context for a specific field, but may require specialized knowledge of the subject matter to interpret correctly, extract, and encode in the EHR or EMR in a structured format.

What are needed are systems and methods that address one or more of these shortcomings.

SUMMARY OF THE INVENTION

In one aspect, the system provides mechanisms for automatically processing clinical documents in bulk, identifying and extracting key characteristics, and generating machine learning models that are refined and optimized through the use of continuous training data.

In another aspect, a method includes the steps of determining a first concept from a text of a medical record from an electronic health record system, the first concept relating to a patient, identifying a match to the first concept in a first list of concepts, wherein the first list of concepts is not a predetermined authority, referencing the first concept with an entity in a database of related concepts, identifying a match to a second concept in a second list of concepts, the second list of concepts not directly linked to the first list of concepts except by a relationship to the entity, wherein the second list of concepts is the predetermined authority, and providing the second concept as an identifier of the patient's medical record.

In still another aspect, a method includes the step of applying a medical ontology to an electronic health record to extract at least one structured field value for the health record.

In yet another aspect, a method for determining whether a patient may be enrolled into a clinical trial includes the steps of examining the patient's medical record from an electronic health record system, deriving a plurality of first concepts from the medical record, normalizing each concept in the plurality of first concepts to produce, for each normalization, a normalized concept, comparing each normalized concept to a list of study criteria, to indicate if the normalized concept meets the criteria, and if each criteria is met, indicating that the patient is not ineligible for enrollment in the clinical trial.

In a further aspect, a method for developing synthetic control arms for clinical trials includes the steps of examining a patient's medical record from an electronic health record system, deriving a plurality of first concepts from the medical record, normalizing each concept in the plurality of first concepts to produce, for each normalization, a normalized concept, comparing each normalized concept to a list of study criteria, to indicate if the normalized concept meets the criteria, and if each criteria is met, indicating that the patient is part of an experimental group for the clinical trial.

In another aspect, a method for institution-wide analysis of data in an electronic health record, comprising, for each of a plurality of patient medical records in an electronic health record system includes the steps of examining the patient medical record, deriving a plurality of first concepts from the medical record, normalizing each concept in the plurality of first concepts to produce, for each normalization, a normalized concept, and analyzing each of the normalized concepts to identify data trends within the institution.

In still another aspect, a method for performing quality checks on information contained in a patient medical record in an electronic health record system includes the steps of examining the patient medical record, deriving a plurality of first concepts from the medical record, normalizing each concept in the plurality of first concepts to produce, for each normalization, a normalized concept, comparing a first normalized concept derived from a first section of the medical record with a second normalized concept derived from a second section of the medical record, and evaluating consistency between the first and second normalized concepts.

In a further aspect, a method for extracting information from an electronic publication includes the steps of examining the publication, deriving a plurality of first concepts from the publication, normalizing each concept in the plurality of first concepts to produce, for each normalization, a normalized concept, and generating a knowledge database comprising each of the normalized concepts.

In yet another aspect, a method for comparing data generated by a first institution and a second institution includes the steps of, for each of a plurality of patient medical records in an electronic health record system of the first institution, examining the patient medical record, deriving a plurality of first concepts from the medical record, and normalizing each concept in the plurality of first concepts to produce, for each normalization, a normalized first concept. The method also includes, for each of a plurality of patient medical records in an electronic health record system of the second institution, examining the patient medical record, deriving a plurality of second concepts from the medical record, and normalizing each concept in the plurality of first concepts to produce, for each normalization, a normalized second concept. Still further, the method includes comparing the normalized first concepts with the normalized second concepts.

BRIEF DESCRIPTION OF THE DRAWINGS

FIG. 2 is an exemplary table representing a structured result;

FIG. 4 is an exemplary word weighing representation according to an embodiment;

FIG. 5 is an exemplary sequence labeling classification representation according to an embodiment;

DETAILED DESCRIPTION OF THE DISCLOSURE

Figure 1:
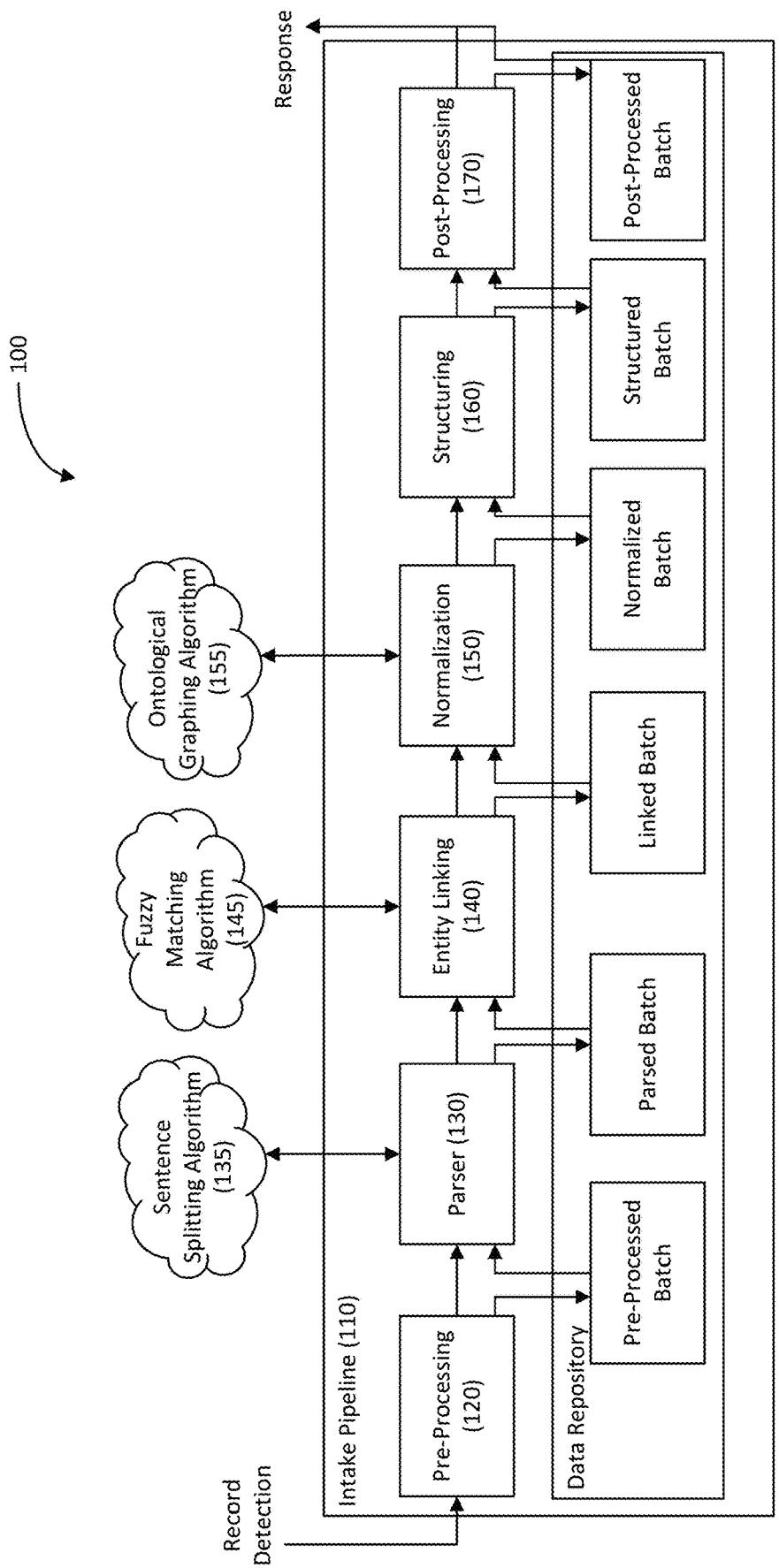
FIG. 1 is an exemplary pipeline for processing electronic records into structured results.

In one aspect, a system is disclosed that identifies information in clinical documents or other records. The system may use a combination of text extraction techniques, text cleaning techniques, natural language processing techniques, machine learning algorithms, and medical concept (Entity) identification, normalization, and structuring techniques. The system also maintains and utilizes a continuous collection of training data across clinical use cases (e.g., diagnoses, therapies, outcomes, genetic markers, etc.) that help to increase both accuracy and reliability of predictions specific to a patient record. The system accelerates a structuring of clinical data in a patient's record. The system may execute subroutines that highlight, suggest, and pre-populate an electronic medical record ("EHR" or "EMR"). The system may provide other formats of structured clinical data, with relevant medical concepts extracted from the text and documents of record.

One embodiment may include an ontology-directed system that specializes in abstracting patient from fields from that particular ontology. Additionally or alternatively, the system may have aspects that are ontology agnostic for performing recognition across multi-discipline medical records.

The system may include a persistent, stateless service that receives a plurality of queued messages from one or more peripheral services (e.g., a file conversion service or an optical character recognition service) which may also perform natural language processing (NLP) operations on outputs of those peripheral services. Those NLP operations include machine learning features, as described herein, in order to increase the speed, efficiency, and accuracy of the processing. A persistent, stateless system is a system operating in an asynchronous manner in comparison to a conventional point to point pipeline. For example, the system may be structured in a "pipeline" fashion, but each modular component of the system may retrieve and store exemplary input/output datasets as they become available, without relying on the modular component before or after in the pipeline to initiate or acknowledge availability for a transfer. Such statelessness allows for more advanced parallelization because it reduces inefficiencies at each bottleneck of the pipeline (i.e., handshaking to pass data). More detail on the persistent, stateless service is discussed with reference to FIG. 1 below.

The system may include a training service designed to promote user interaction to improve machine learning capabilities. In one aspect, the training service may use a production repository as its input data. In another aspect, the training service may use a data repository separate from the production repository. Additionally, the system may operate in a plurality of manners. In a first manner, the system may be triggered in response to specific queries requesting processing on specific EHR or EMR files. In a second manner, the system may include a backend service that reviews and processes EHR or EMR files continuously (i.e., without a need for specific user queries). The backend service may operate asynchronously from user input, such as queries or commands. In such a manner, the system may detect when a patient record has been received, either partially or in full, and begin processing the patient record in aggregate or as a whole to determine relevant medical concepts for entry into the EMR.

Definitions

As used herein, the following terms should be understood to have their plain and ordinary meanings to one of ordinary skill in the relevant art. To wit:

"Concept," in its broadest sense, means a phrase of interest. Concepts, more particularly, may include clinical or medical concepts, which are clinically defined terms within a medical ontology or synonyms or variants thereof.

A "list of concepts" means a grouping of two or more concepts.

A "predetermined authority" means a vocabulary, terminology, ontology, code set, or other manner of recording or representing data, such as clinical or medical data, that has been established or decided in advance.

A "related concept" means a concept shared within a vocabulary, terminology, ontology, code set, or other manner of recording or representing data in fields of clinical or medical data such as a diagnosis, procedure, medication, treatment, or other data.

"Directly linked" means having a formal, defined mapping between elements, e.g., a parent-child relationship, an "is a,", "type of," "broader than," or "narrower than" relationship, a synonym relationship, or some other type of predetermined or predefined relationship.

A "structured format" means a format that is standardized, normalized, modeled, or otherwise organized to make it searchable using computer-based search engine tools.

To "extract a field from a structured format" means to generate a separate data object, the contents of which match or otherwise are derived from a specific, identified portion of the structured data.

A "predetermined degree of specificity" means a closeness of match or fit that has been established or decided in advance.

"Selection criteria" means those factors or standards by which certain data is evaluated.

"Normalizing a concept" means converting a concept from an unstructured format to a structured format or from one structured format to a second, different structured format.

In the field of clinical abstraction from EHR and EMR documents, machine learning or deep learning may be combined with NLP techniques to abstract relevant medical concepts. While the detailed implementations of these are disclosed in more detail below, an exemplary abstraction performed on a simple text is now provided to give a general understanding of one aspect of the disclosure. For instance, the simple text "The patient was given Tylenol 50 mg at 10:35 am." may be analyzed using a machine learning algorithm (MLA) trained on EHR and EMR documents relating to thousands of patients to recognize medications that the patient was prescribed in order to generate the table of FIG. 2.

Generating a training set from which to train the MLA involves both enumerating known drugs (which may include thousands or even tens of thousands of drugs) and also maintaining the flexibility to recognize drugs which are not included in the sources of the known drugs. The process of enumerating the known drugs into a list may include identifying clinical drugs prescribed by healthcare providers, pharmaceutical companies, and research institutions. Such providers, companies, and institutions may provide reference lists of their drugs. For example, the US National Library of Medicine (NLM) publishes a Unified Medical Language System (UMLS) including a Metathesaurus having drug vocabularies including CPT®, ICD-10-CM, LOINC®, MeSH®, RxNorm, and SNOMED CT®. Each of these drug vocabularies highlights and enumerates specific collections of relevant drugs. Other institutions such as insurance companies may also publish clinical drug lists providing all drugs covered by their insurance plans. By aggregating the drug listings from each of these providers, companies, and institutions, an enumerated list of clinical drugs that is universal in nature may be generated.

A combination of NLP and supervised, semi-supervised, or unsupervised MLA techniques may be used to generate an intelligent training set of data to recognize entries from the enumerated list of clinical drugs, in order to identify patterns within the text of abstracted documents which typically surround drug entries. The identified patterns may then be applied to unknown drugs to generate new entries which are added to the clinical drug list. An exemplary pattern may be a sentence structure containing "patient was given _____" or "patient was prescribed _____." In these examples, the known drugs are the supervised portion of the semi-supervised algorithm while the new entries determined are the unsupervised portion of the semi-supervised algorithm. In this manner, a non-exhaustive listing of drugs may be leveraged to train a MLA to detect drugs based on sentence structure, associated key terms, or other patterns in the text. Once trained, the unsupervised portion of the semi-supervised algorithm will apply the training to detect unclassified words for addition to the classification list. In this manner, a semi-supervised MLA can apply features of NLP to detect and classify unknown and known drug entries in medical texts. While described herein with respect to the medical concept of a drug, this approach may be applied to all medical concept classifications using the techniques described herein. Specific details of the NLP and MLA techniques are discussed in more detail with respect to FIGS. 3-7, below. Specific details of supervised, semi-supervised, or unsupervised MLA techniques are discussed in more detail below.

Medical data may include numerous fields including, but not limited to, patient demographics (e.g., patient name, date of birth, gender, ethnicity, date of death, address, smoking status, diagnosis dates, personal medical history, family medical history, etc.), clinical diagnoses (e.g., date of initial diagnosis, date of metastatic diagnosis, cancer staging, tumor characterization, tissue of origin, etc.), treatments and outcomes (e.g., therapy groups, medications, surgeries, radiotherapy, imaging, adverse effects, associated outcomes, and corresponding dates, etc.), and genetic testing and laboratory information (e.g. genetic testing, performance scores, lab tests, pathology results, prognostic indicators, and corresponding dates, etc.). Each of the fields (e.g., address, cancer staging, medications, genetic testing, etc.) may also have a plurality of subfields. For example, address may have subfields for type of use (e.g., personal, business), street, city, state, zip, country, and a start or end date (i.e., date that residency at the address begins or expires). Genetic testing may have subfields for the date of genetic testing, testing provider used, test method (e.g., genetic sequencing method, gene panel), gene results (e.g., included genes, variants, expressions, etc.), tumor mutational burden, and microsatellite instability. The above provided examples, enumerations, and lists are not intended to limit the scope of the available fields and are intended to convey only the nature and structure that fields within medical data may be represented within a universal EMR. These fields of medical data may also identify concept candidates, discussed in more detail below with respect to FIGS. 3-7. In an exemplary embodiment, categorization of concept candidates may include: Diagnosis, Primary Diagnosis Site, Metastatic Diagnosis Site, Tumor Characterization, Standard Grade, Alternative Grade, Medications, Surgical Procedure, Smoking Status, Comorbidities, Adverse Events, Outcomes, Performance Scores, Radiotherapy Modality, Radiotherapy Units, Imaging Type, Gene Mention, Immunology Markers, TNM Status, and American Joint Committee on Cancer (AJCC) Stage. In one example, Tylenol may be a concept candidate relating to the Medications or Outcomes category as a medication in treatment or a medication in outcomes.

With respect to abstraction, a patient data store such as the data repository of FIG. 1 may include one or more feature modules which may comprise a collection of features available for every patient in the system. While feature scope across all patients is informationally dense, a patient's feature set may be sparsely populated across the entirety of the collective feature scope of all features across all patients. For example, the feature scope across all patients may expand into the tens of thousands of features while a patient's unique feature set may only include a subset of hundreds or thousands of the collective feature scope based upon the records available for that patient. After abstraction, these features may be used to generate and model the artificial intelligence classifiers in the system. Therefore, it is important that the abstraction include modalities for detection and structuring of a complete feature set. For example, in a cancer ontology abstraction engine, the following list of features may be supported.

Feature collections may include a diverse set of fields available within patient health records. Clinical information may be based upon fields which have been entered into an electronic medical record (EMR) or an electronic health record (EHR) by a physician, nurse, or other medical professional or representative. Other clinical information may be curated from other sources, such as molecular fields from genetic sequencing reports. Sequencing may include next-generation sequencing (NGS) and may be long-read, short-read, or other forms of sequencing a patient's somatic and/or normal genome. A comprehensive collection of features in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may comprise molecular data features, such as features derived from an RNA feature module or a DNA feature module sequencing.

Another subset of features, imaging features from imaging feature module, may comprise features identified through review of a specimen through pathologist review, such as a review of stained H&E or IHC slides. As another example, a subset of features may comprise derivative features obtained from the analysis of the individual and combined results of such feature sets. Features derived from DNA and RNA sequencing may include genetic variants from variant science module which are present in the sequenced tissue. Further analysis of the genetic variants may include additional steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology features.

Features derived from structured, curated, or electronic medical or health records may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates to any of the above.

Features may be derived from information from additional medical or research based Omics fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features derived from imaging data may further include reports associated with a stained slide, size of tumor, tumor size differentials over time including treatments during the period of change, as well as machine learning approaches for classifying PDL1 status, HLA status, or other characteristics from imaging data. Other features may include the additional derivative features sets from other machine learning approaches based at least in part on combinations of any new features and/or those listed above. For example, imaging results may need to be combined with MSI calculations derived from RNA expressions to determine additional further imaging features. In another example a machine learning model may generate a likelihood that a patient's cancer will metastasize to a particular organ or a patient's future probability of metastasis to yet another organ in the body. Other features that may be extracted from medical information may also be used. There are many thousands of features, and the above listing of types of features are merely representative and should not be construed as a complete listing of features.

An alteration module may be one or more microservices, servers, scripts, or other executable algorithms which generate alteration features associated with de-identified patient features from the feature collection. Alterations modules may retrieve inputs from the feature collection and may provide alterations for storage. Exemplary alterations modules may include one or more of the following alterations as a collection of alteration modules. An SNP (single-nucleotide polymorphism) module may identify a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underline differences in our susceptibility to a wide range of diseases (e.g.—sickle-cell anemia, β-thalassemia and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome. An InDels module may identify an insertion or deletion of bases in the genome of an organism classified among small genetic variations. While usually measuring from 1 to 10 000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites. An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs). A TMB (tumor mutational burden) module may identify a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials. A CNV (copy number variation) module may identify deviations from the normal genome and any subsequent implications from analyzing genes, variants, alleles, or sequences of nucleotides. CNV are the phenomenon in which structural variations may occur in sections of nucleotides, or base pairs, that include repetitions, deletions, or inversions. A Fusions module may identify hybrid genes formed from two previously separate genes. It can occur as a result of: translocation, interstitial deletion, or chromosomal inversion. Gene fusion plays an important role in tumorgenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates the prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer. An IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualising an antibody-antigen interaction can be accomplished in a number of ways. In the most common instance, an antibody is conjugated to an enzyme, such as peroxidase, that can catalyse a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated. A Therapies module may identify differences in cancer cells (or other cells near them) that help them grow and thrive and drugs that "target" these differences. Treatment with these drugs is called targeted therapy. For example, many targeted drugs go after the cancer cells' inner 'programming' that makes them different from normal, healthy cells, while leaving most healthy cells alone. Targeted drugs may block or turn off chemical signals that tell the cancer cell to grow and divide; change proteins within the cancer cells so the cells die; stop making new blood vessels to feed the cancer cells; trigger your immune system to kill the cancer cells; or carry toxins to the cancer cells to kill them, but not normal cells. Some targeted drugs are more "targeted" than others. Some might target only a single change in cancer cells, while others can affect several different changes. Others boost the way your body fights the cancer cells. This can affect where these drugs work and what side effects they cause. Matching targeted therapies may include identifying the therapy targets in the patients and satisfying any other inclusion or exclusion criteria. A VUS (variant of unknown significance) module may identify variants which are called but cannot be classify as pathogenic or benign at the time of calling. VUS may be catalogued from publications regarding a VUS to identify if they may be classified as benign or pathogenic. A Trial module may identify and test hypotheses for treating cancers having specific characteristics by matching features of a patient to clinical trials. These trials have inclusion and exclusion criteria that must be matched to enroll which may be ingested and structured from publications, trial reports, or other documentation. An Amplifications module may identify genes which increase in count disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another. An Isoforms module may identify alternative splicing (AS), the biological process in which more than one mRNA (isoforms) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternative spliced isoforms. A Pathways module may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations. A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing.

Structural variant classification may include evaluating features from the feature collection, alterations from the alteration module, and other classifications from within itself from one or more classification modules. Structural variant classification may provide classifications to a stored classifications storage. An exemplary classification module may include a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules. A classifier for clinical trials may include evaluation of variants identified from the alteration module which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. Similar classifications may be performed for therapies, loss-of-function, gain-of-function, diagnosis, microsatellite instability, tumor mutational burden, indels, SNP, MNP, fusions, and other alterations which may be classified based upon the results of the alteration modules.

Each of the feature collection, alteration module(s), structural variant and feature store may be communicatively coupled to a data bus to transfer data between each module for processing and/or storage. In another embodiment, each of the feature collection, alteration module(s), structural variant and feature store may be communicatively coupled to each other for independent communication without sharing the data bus.

In addition to the above features and enumerated modules. Feature modules may further include one or more of the following modules within their respective modules as a sub-module or as a standalone module.

Germline/somatic DNA feature module may comprise a feature collection associated with the DNA-derived information of a patient or a patient's tumor. These features may include raw sequencing results, such as those stored in FASTQ, BAM, VCF, or other sequencing file types known in the art; genes; mutations; variant calls; and variant characterizations. Genomic information from a patient's normal sample may be stored as germline and genomic information from a patient's tumor sample may be stored as somatic.

An RNA feature module may comprise a feature collection associated with the RNA-derived information of a patient, such as transcriptome information. These features may include raw sequencing results, transcriptome expressions, genes, mutations, variant calls, and variant characterizations.

A metadata module may comprise a feature collection associated with the human genome, protein structures and their effects, such as changes in energy stability based on a protein structure.

A clinical module may comprise a feature collection associated with information derived from clinical records of a patient and records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

An imaging module may comprise a feature collection associated with information derived from imaging records of a patient. Imaging records may include H&E slides, IHC slides, radiology images, and other medical imaging which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

An epigenome module, such as epigenome module from Omics, may comprise a feature collection associated with information derived from DNA modifications which are not changes to the DNA sequence and regulate the gene expression. These modifications are frequently the result of environmental factors based on what the patient may breathe, eat, or drink. These features may include DNA methylation, histone modification, or other factors which deactivate a gene or cause alterations to gene function without altering the sequence of nucleotides in the gene.

A microbiome module, such as microbiome module from Omics, may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

A proteome module, such as proteome module from Omics, may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) may also be included in Omics, such as a feature collection associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous image sequence, or video, can be interpreted as the capture of a single image evolving through time of mutations revealing patient insights.

A sufficiently robust collection of features may include all of the features disclosed above; however, models and predictions based from the available features may include models which are optimized and trained from a selection of features that are much more limiting than the exhaustive feature set. Such a constrained feature set may include as few as tens to hundreds of features. For example, a model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup.

A feature store may enhance a patient's feature set through the application of machine learning and analytics by selecting from any features, alterations, or calculated output derived from the patient's features or alterations to those features. Such a feature store may generate new features from the original features found in feature module or may identify and store important insights or analysis based upon the features. The selections of features may be based upon an alteration or calculation to be generated, and may include the calculation of single or multiple nucleotide polymorphisms insertion or deletions of the genome, a tumor mutational burden, a microsatellite instability, a copy number variation, a fusion, or other such calculations. An exemplary output of an alteration or calculation generated which may inform future alterations or calculations includes a finding of hypertrophic cardiomyopathy (HCM) and variants in MYH7. Wherein previous classified variants may be identified in the patient's genome which may inform the classification of novel variants or indicate a further risk of disease. An exemplary approach may include the enrichment of variants and their respective classifications to identify a region in MYH7 that is associated with HCM. Any novel variants detected from a patient's sequencing localized to this region would increase the patient's risk for HCM. Features which may be utilized in such an alteration detection include the structure of MYH7 and classification of variants therein. A model which focuses on enrichment may isolate such variants.

The above referenced artificial intelligence models may be gradient boosting models, random forest models, neural networks (NN), regression models, Naive Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

An abstraction system, such as the system of FIG. 1 may support any of the features detailed herein. For the purposes of illustrating the capabilities of the intake pipeline for extracting information from patient records and populating structured fields, the following exemplary feature abstractions are provided.

As seen in FIG. 2, the sentence "The patient was given Tylenol 50 mg at 10:35 am." in a document dated Jan. 1, 2001, may be encoded field-by-field by identifying and populating one or more fields of:

Text: The entirety of the text (i.e., "The patient was given Tylenol 50 mg at 10:35 am.").

Medication: Identifying any medication mentioned in the text (i.e., Tylenol). Medications may be brand name or generic name. This field does not include information about the dosage or method of administration.

Active Ingredient: Identifying the active ingredients (i.e., acetaminophen) of the medication mentioned using a list such as a search table linking drug names to their active ingredients.

Dosage & Dosage Units: The dosage (i.e., 50 mg) associated with the medication mentioned. In the above example, identifying that the dosage as 50 mg is fairly straightforward by reading the sentence, but clinical data is often printed in tables with a variety of structures that are not easy to infer. As such, normalizing the dosage and dosage units by separating value 50 into the dosage field and string "mg" or by selecting a known value entry for the milligram units within a list may be preferable.

Document & Page: The document and page where the text is found (i.e., Progress Note 01_01_01.pdf and page 3).

UMLS_CUI: The Concept Unique Identifier (CUI) field (i.e., C1234567) of the UMLS entry corresponding to the medication. The UMLS is a list of medical concepts (described in more detail with respect to FIG. 7, below) and the UMLS_CUI refers to the CUI field, which is UMLS' universal identifier. UMLS is comprised of a number of independently maintained clinical dictionaries and ontologies (e.g., those for cancer diagnosis & treatment, dentistry, veterinarian medicine, etc.). That is, the CUIs are universal to UMLS, e.g., there is only one CUI for Tylenol across all of its constituent dictionaries that enables UMLS to unite all of these disparate sources.

UMLS_AUI: The Atom Unique Identifier (AUI) field (i.e., RXNORM #12345) is the dictionary-specific identifying code of the UMLS. Where the CUI is universal, and has the same entry across all included sources, the AUI for Tylenol will have different AUIs for each dictionary that it has an entry in.

In an alternate embodiment, structured data for a procedurally focused conversion of data may include receiving the sentence "The patient underwent a lumpectomy to remove an area of Ductal Carcinoma in Situ." in a document dated Jan. 1, 2001, which may be encoded field-by-field by identifying and populating one or more fields of:

Text: The entirety of the text (i.e., "The patient underwent a lumpectomy to remove an area of Ductal Carcinoma in Situ.").

Procedure: The surgical procedure performed on the patient. This may be a canonical name (i.e. Lumpectomy) or synonym (e.g. Breast conservation surgery).

Diagnosis: The condition which the surgery aims to treat (i.e. Ductal Carcinoma in Situ).

Document & Page: The document and page where the text is found (i.e., Progress Note 01_01_01.pdf and page 5).

UMLS_CUI: The Concept Unique Identifier (CUI) field (i.e., C1234568) of the UMLS entry corresponding to the procedure.

UMLS_AUI: The Atom Unique Identifier (AUI) field (i.e., RXNORM #12346) is the dictionary-specific identifying code of the UMLS. Where the CUI is universal, and has the same entry across all included sources, the AUI for Lumpectomy will have different AUIs for each dictionary that it has an entry in.

In yet another embodiment, structured data for a treatment focused conversion of data may include receiving the sentence "After the patient's lumpectomy to remove an area of Ductal Carcinoma in Situ, they will receive brachytherapy." in a document dated Jan. 1, 2001, may be encoded field-by-field by identifying and populating one or more fields of:

Text: The entirety of the text (i.e., "After the patient's procedure, they will receive brachytherapy.").

Radiotherapy Modality: The type of radiotherapy that the patient will receive (i.e. Brachytherapy).

Document & Page: The document and page where the text is found (i.e., Progress Note 01_01_01.pdf and page 6).

UMLS_CUI: The Concept Unique Identifier (CUI) field (i.e., C1234569) of the UMLS entry corresponding to the radiotherapy modality.

UMLS_AUI: The Atom Unique Identifier (AUI) field (i.e., RXNORM #12348) is the dictionary-specific identifying code of the UMLS. Where the CUI is universal, and has the same entry across all included sources, the AUI for Brachytherapy will have different AUIs for each dictionary that it has an entry in.

Structured data for another therapy focused conversion of data may include the sentence "The patient will receive hormone therapy once daily for a period of 5 years." in a document dated Jan. 1, 2001, which may be encoded field-by-field by identifying and populating one or more fields of:

Text: The entirety of the text (i.e., "The patient will receive hormone therapy once daily for a period of 5 years.").

Treatment: The treatment the patient will receive (i.e. hormone therapy).

Frequency: The frequency of applications of this treatment (i.e. once daily).

Duration: The duration of this round of treatment (i.e. 5 years).

Document & Page: The document and page where the text is found (i.e., Progress Note 01_01_01.pdf and page 6).

UMLS_CUI: The Concept Unique Identifier (CUI) field (i.e., C1234570) of the UMLS entry corresponding to the treatment.

UMLS_AUI: The Atom Unique Identifier (AUI) field (i.e., RXNORM #12349) is the dictionary-specific identifying code of the UMLS. Where the CUI is universal, and has the same entry across all included sources, the AUI for hormone therapy will have different AUIs for each dictionary that it has an entry in.

In one instance, the above fields may be populated by a data analyst with sufficient medical knowledge and access to the requisite databases. Such an analyst may apply their education and experiences in the field of medicine to identify any medications administered despite confounding factors present in the text (e.g., shorthand, typos, obscure references), their dosage, and understand the integration of the two in the provided text. However, analysts are constrained by their human limits. Actions such as locating the data, opening it up in either a physical or digital format, reading through documents of 100 s or 1000 s of pages, etc. all require considerable time. Furthermore, the companies and institutions which hire analysts must invest in considerable financial expenses to hire, train, and maintain teams of analysts. Incorporating a combination of machine learning algorithms (MLA) and natural language processing (NLP) algorithms into this process may substantially improve the efficiency of the analysts or replace them altogether. The MLA and NLP algorithms will be discussed in more detail with respect to FIGS. 3-7, below. Before text may pass through the multiple layers of MLA and NLP algorithms, it must be extracted from the documents using optical character recognition (OCR) and cleaned up through a variety of pre-processing steps.

Turning now to FIG. 1, a high level overview of an exemplary processing pipeline 100 is provided. An exemplary Intake Pipeline 110 may be configured to perform the following processing steps: 1. OCR, 2. Pre-processing, 3. Sentence Splitting, 4. Candidate Extraction, 5. Entity Linking, 6. Entity Normalization, and 7. Entity Structuring. Specifically, and with reference to FIG. 1, pipeline stage 120 for pre-processing may include OCR and text cleaning, stage 130 for parsing may include NLP algorithms for sentence splitting and candidate extraction, stage 140 for dictionary lookups may include entity linking, stage 150 for normalization may include entity normalization, stage 160 for structuring may include entity structuring, and stage 170 for post-processing may include structuring the data and formatting it into a universal EMR or institution based EMR format. Due to the asynchronous and modular nature of the pipeline stages, each stage may pass data directly to the next stage based on processing availability or may store data in a corresponding portion of a storage component or database. Batching or caching may be leveraged to provide additional time and resource reductions as cached results may be stored in the data repository for importing directly into an updated pipeline stage rather than reprocessing all records through the whole pipeline. In an exemplary embodiment, a sentence splitting algorithm may be stored in a cloud-based server or on a local/remote server 135 and may be incorporated into the parser at stage 130. A sentence splitting algorithm may be incorporated directly into the parser at stage 130 and invoked as a subroutine. A fuzzy matching algorithm 145 may be incorporated into the dictionary lookup at stage 140. In lieu of a fuzzy matching algorithm, a dictionary lookup algorithm with hardcoded alternatives may be implemented at stage 140. An Ontological graphing algorithm 155 may be incorporated into the normalization at stage 150. In lieu of an ontological graphing algorithm 155, normalization at stage 150 may include a second dictionary lookup algorithm with hardcoded mappings to relevant concepts. In other embodiments, hardcoded mappings and/or alternatives may be identified in real time during processing by comparing mappings and alternatives to a selection criteria, such as those mappings and alternatives which are located in pre-approved databases.

For example, upon receiving a record update or a request in the form of a clinical document, a database of multiple documents, or another form of patient record, the request may pass through a pre-processing subroutine, a parsing subroutine, a dictionary lookup subroutine, a normalization subroutine, a structuring subroutine for filtering and/or ranking, and a post-processing subroutine in order to generate and serve a response to a remainder of the system. The first four of these subroutines may encompass a first layer, in which the system identifies and structures clinical concepts with corresponding metadata (i.e., clinical or medical concepts) extracted from clinical documents.

The intake pipeline 110 receives a clinical document that may include machine readable text or that may be received as an image file. If necessary, the document may be submitted to a pre-processor stage 120 that performs text cleaning and error detection (i.e., format conversion, resolution conversion, batch sizing, text cleaning, etc.). Once pre-processed, the document may be submitted for OCR on the document to convert the text into a machine-readable format (i.e., text document, html, etc.). Once in a machine-readable format, the error correction (e.g., spell checking, noise removal, context based correlation, etc.) may be performed on the now-machine-readable text. The intake pipeline stages 120-150 are modular components, which allows for real-time selection of the best processing tools and software depending on the type of document and document content being processed, enabling the processing pipeline to replace/compare algorithms used as necessary. Two examples of OCR software that may be used include Tesseract and Google Cloud Vision API. Tesseract provides high-speed OCR for documents which do not have any artifacting/noise (i.e., documents that have been printed to PDF or that had very little noise generated during the scanning process). Google Cloud Vision API, conversely, may be used for documents which have too much noise, as it is well-suited to process old documents or images of documents that have been scanned/faxed many times, introducing extensive artifacting and noise into the image. As a result, Cloud Vision may provide detailed information about the position of paragraphs, words, and documents within the documents processed. Other OCR systems may also be utilized in lieu of or in combination with the two described above.

The modularity of each processing stage requires different pre-processing mechanisms for each OCR service/software implemented. For example, different OCR services support some image formats and resolutions for OCR but may not support others. When processing patient records, many document formats included within the record are unsupported, and may require format conversion from the unsupported format to a support format. Exemplary conversions may take documents of a variety of formats (PDF, PNG, JPG, etc.) and convert them to a format that each respective OCR service accepts (e.g., JPG, PNG, etc.). During format conversion, additional processing may be performed for parameter optimization for each respective document to achieve the best results from the OCR service selected (e.g. converting documents from a source resolution to a resolution [dpi] best supported, combining multiple requests into one to optimize batch processing). For example, when utilizing Google Cloud Vision, images may need to be format-converted to 300 dpi JPG files. Furthermore, Google Cloud Vision API charges for OCR on a per-request basis, but supports requests of up to 4 MB and supports batch requests (i.e. including as many images as can fit in one 4 MB requests) for no extra cost. Additional processing may be performed to include additional document images into a request to place each request at the maximum file size and use batch processing to decrease costs.

Documents received at the pre-preprocessing stage may be in various text formats (e.g. DOC, DOCX, RTF, or as values in a spreadsheet/database). For simple documents, pre-processing may be performed by simply extracting any text directly (e.g., TXT, RTF, etc.), but some require advanced software to parse the file formats (e.g. DOCX, PDF, ACCDB). Exemplary software for parsing more complex file formats include pandoc and PDFBox.

In another embodiment, additional pre-processing may be performed after submitting an image to OCR to determine whether the detected text is "reasonable" before outputting final results. While some OCR technologies may perform their own reasonability determination, it may be necessary to further improve upon the quality of the OCR output by performing a text cleaning algorithm on the OCR output. Text cleaning may be implemented by a category of NLP models designed for Language Modeling. Additionally, machine learning algorithms and deep learning algorithms may be utilized to further improve upon the OCR results. Exemplary categories of language models may include: statistical (n-gram), graphical (CRF/HMM), and neural (RNN, LSTM, skipgram, BOW, etc.). While each category of language model may process datasets of particular structure and content differently, the modular nature of the processing pipeline allows the most appropriate language model to be selected based upon the document being processed. For instance, a first language model may be selected if the document is a progress note while a second language model may be selected if the document is a lab result. As another example, a first language model may be selected if the document is from a first institution and a second language model may be selected if the document is from a second institution. As another example, a first language model may be selected if the document is from a first clinician and a second language model may be selected if the document is from a second clinician.

In one aspect, due to the frequency of tables, charts, structured headers, and other features in medical documents, neural language models may be preferred. Neural networks for language modeling may be trained over millions of sentences and perform best when trained over text from the same domain as they will encounter in a production system. For example, language models trained over medical/clinical text will perform better in medical-based OCR text cleaning tasks than language models trained over online reviews, news articles, or other generic and freely-available sources. Similarly, language models trained over clinical documents that are specific to a particular disease state, such as cancer, may perform better in medical-based OCR text cleaning tasks upon disease state-related clinical documents than language models trained over clinical documents that are not specific to a particular disease state. By providing a training set having millions of clinical documents that are similar to the documents submitted for OCR, an exemplary language model may be trained over in-domain text that many traditional NLP sources do not have access to, resulting in a more robust language model.

Language models may estimate the probability of a given sequence of words or characters (letters, numbers, punctuation, etc.) occurring in a current document based on the frequency of the given sequence of words or characters as they appeared in the original training documents. Language models may identify regions of OCR output that are uncommon in the training text (e.g. "stage iv beast cancer" is an unlikely sequence of words in medical documents). Language models may also identify which words/characters were most likely to have occurred in each position in text, for example, "stage iv _____ cancer" may have a high probability for "lung" and "breast" filling the blank. By combining a probability distribution over words most likely to fill the blank (e.g., in this example cancer sites, but may be medications, dates, diagnosis, treatment results, etc.) and words most likely to be OCR as "beast," the system may determine that "beast" was most likely "breast" without having to look at the image itself and only relying on linguistic patterns.

A probability distribution may be generated by applying a neural network for Named Entity Recognition (NER). For example, individual words may be provided a weighting factor for probability of occurrence across a massive training set. Statistical information may be stored that indicate likely phrases, based off a starting word, and any following words of a phrase. Each word, in turn, may be applied a weight about whether it is a starting word or a following word and the likelihood that the word is part of a phrase or standing alone in the text.

In one example, the phrase "stage iv _____ cancer" may be processed. "Stage" may be provided a starting word score of 0.6, a following word score of 0.3, and a standalone score of 0.1 which would account for the entirety of the potential distribution of the word's appearance in the training text. The word "iv" may be provided a starting word score of 0.05, a following score of 0.55, and a standalone score of 0.4. The word "cancer" may be given a starting score of 0.1, a following score of 0.7, and a standalone score of 0.2. A sentence analysis for the exemplary NER may find that because "stage" has a high probability for being a starting word and "iv" has a high probability for being a following word, that "_____" may have a higher probability for being a following word that matches "stage iv _____" or "stage iv _____ cancer" in a phrase.

Additionally, because "cancer" similarly has a high probability for being a following word, NER may predict that the "_____" is either a following word that continues the word beginning at "stage" or may be a beginning word that begins before "cancer". Because the word "beast" has a beginning word score of 0.1, a following score of 0.2 and a standalone score of 0.7, the model may flag that "beast" does not fit within the expected sequence of words. By comparing similar words, (e.g., breast, feast, rest, roast, wrest, etc.) the NER model may identify that breast has a beginning score of 0.5, a following score of 0.3, and a standalone score of 0.2, making breast fit within two models of the predicted phrases and selecting "breast" to replace "beast" based on the predicted phases alone. The modified phrase then may be further tested, or tested alone using a more generalized probability distribution. For example, the training date may weight the occurrence of words in medical texts. While the word "beast" may rarely occur in an EMR/EHR, (e.g., patient was mauled by unknown beast), "breast" may occur more frequently (e.g., patient expresses concern re: lump in breast, breast cancer, stage iv breast cancer, patient's breast recovered from surgery, etc.), giving "breast" a much higher probability of occurrence weighting than "beast." As a result, the preprocessing stage 220 may replace "beast" with "breast," terminate pre-processing, and indicate that the resulting text is reasonable.

Figure 7:
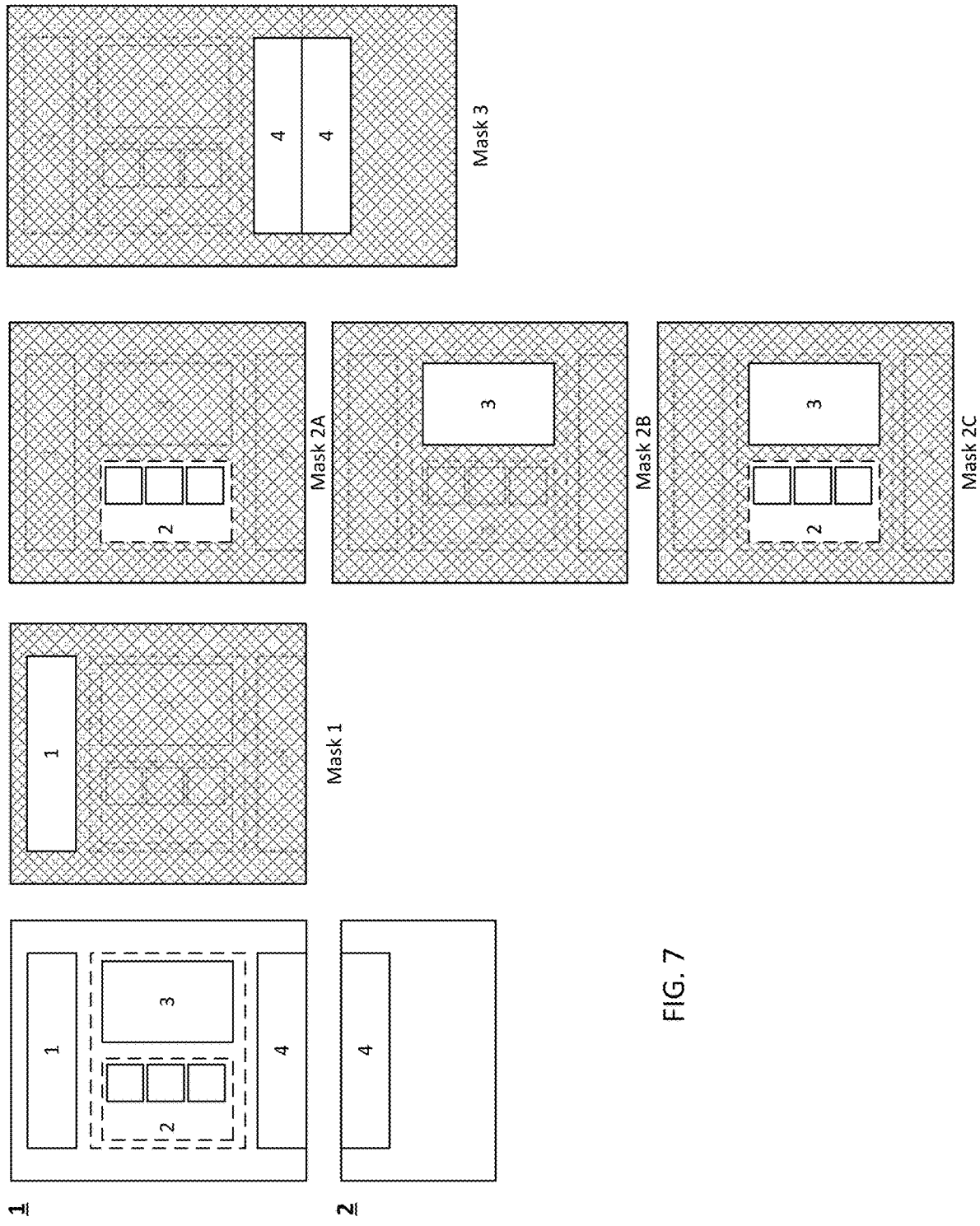
FIG. 7 is an exemplary tabular extraction report and report specific masks.

In an alternate embodiment, a tabular extraction method may be performed across EMR and EHR documents. Tabular extraction involves applying MLA and deep learning algorithms to optimize the OCR process for reports which may have a standardized format. FIG. 7 depicts an exemplary tabular extraction report involving masks 1-3. In this example, a standardized report 710 (e.g., a report used by a physician or group of physicians) may include patient onboarding forms, progress notes, pathology reports, etc. Standardization in this situation may indicate that the reports are presented in a standardized format. For example, a patient onboarding form may have a header which lists patient information such as name, address, symptoms, medications; a progress note may have a table which allows the physician to catalog treatment options recommended to the patient, treatment options which were pursued from a previous visit, and any updates to the status of the patient relating to the treatment options pursued; or a pathology report may include a first section listing a plurality of genetic variants which may be tested in a specific pathology assay and a second section, which may be distinct from the first section, providing sequencing results for each corresponding genetic variant of the first section at a spatially corresponding location to the first section. Furthermore, some reports may feature tables, charts, or other sections which may expand across multiple pages. In this context, an MLA or deep learning neural network (DLNN) may receive a training dataset with annotations for each type of classification that may be performed, and it should be understood that the terms MLA and DLNN are interchangeable throughout this disclosure. Thus, a mention of MLA may include a corresponding DLNN or a mention of DLNN may include a corresponding MLA. A resulting ruleset or neural network may recognize features across a standardized report signifying that a classification may be extracted from a specific section of a particular report. Exemplary metrics and features which may be applied are discussed in more detail below.

An exemplary report featuring Sections 1-4 as described in FIG. 7 may be processed by an MLA or DLNN to identify Section 1 as a header which lists patient demographics such as name and date of birth, Section 2 as a listing of genetic variants which are linked to Section 3, Section 3 as a corresponding sequencing result, and Section 4 as a multi-page table summarizing conclusions made from the sequencing results. One exemplary technique to access the data within each of the identified sections may be to generate a mask which outlines the section, apply the mask to the document to extract each section in turn, and then provide the section to an OCR algorithm (e.g., an OCR post-processing optimized to extracting information from the respective section type).

Exemplary masks for extracting each of the Sections 1-4 are disclosed in FIG. 7. Mask 1 may identify the bounds of Section 1 (e.g., by identifying a size, shape, and origin point for a mask or by identifying a starting ending point of a rectangular mask). The mask may be 1 for the white region or 0 for the black region. The pixel values of the document then may be multiplied with the corresponding mask value to apply the mask or may be applied in a binary fashion with an AND operation. For example, only the region of the image which is multiplied, or AND operation, with a 1 are kept for OCR; the region that is multiplied, or AND operation, with a 0 is lost. Once the mask is applied, an exemplary optimized OCR post-processing for that section may include a regular expression (e.g., "Name:", "DOB:", etc.), and/or a column, row pair(s) which contains key health information (e.g., Column 2, Row 2=Name; Column 2, Row 3=birth date; etc.). In a similar fashion, Section 2 may be extracted next using a second mask and Section 3 may be extracted using a third mask. Sections 2 and 3 may then be supplied to OCR post-processing for linking the results of Section 3 to the enumerated content of Section 2. In an alternate embodiment, Sections 2 and 3 may be extracted at the same time using a combined mask. Section 4 may similarly be extracted at the same time using a combined mask by appending/concatenating the image of page 1 and page 2 together or may be masked individually for each page and the resulting masked sections may be appended/concatenated for post processing.

Given enough processing power and time, the MLA or DLNN performing tabular extraction may be implemented as a single training set for all documents, or it may be segmented into one or more layers to improve processing speed of the extraction process and to allow modular improvements to be incorporated without retraining the entire process at once. An exemplary multi-layer extraction may be performed through a template-based approach using a supervised or semi-supervised training set or may be performed through a fully tabular approach using an unsupervised or semi-supervised training set. In an exemplary template-based approach, an MLA may be provided with specific forms containing a standardized layout for each document type commonly found in the EMR or EHR repositories. Additional information on how to identify the form may be provided (e.g., a location/bound to OCR and a text string to match a document name). In another embodiment, the MLA may train to discern how to identify the form and may train to recognize concept candidates in the specific form document provided. The template-based approach may further incorporate the methods and processes of the tabular approach to operate consistent with the below description.

In an exemplary tabular approach, a first layer of a multi-layered MLA may process the EMR and EHR documents to identify documents of similar form, layout, or structure. For example, in an EMR of a 1000 documents, the first layer MLA may identify that 400 of the documents follow a first similar form (e.g., FIG. 7 form document), 300 follow a second similar form different from the first, and the remaining documents do not follow a similar form. The MLA may identify one or more of a first subset of masks for the 400 documents of first similar form and may identify one or more of a second subset of masks for the 300 documents of a second similar form (e.g., according to the method as disclosed above). An output of the MLA from the first layer may be a series of masks for each of the identified similar forms (e.g., masks 1-3 from FIG. 7). In another embodiment, the first layer may be broken up into a series of MLA; for example, the processing flow of the first layer may be arranged to divide the tasks of recognizing similar documents to identify a potential template and then process each template to generate masks for each of the identified templates as two or more operations.

A second layer of a multi-layered MLA then may utilize the resulting masks from the first layer to process the training data set by identifying regions of interest in a document, identifying a corresponding mask for each identified region of interest, and applying the mask to each document to extract and process the region of interest. An exemplary intermediary processing step of the second layer MLA may identify, for each region of interest, which type of feature the region of interest may contain (e.g., a table, header, graph, etc.). An output of the MLA from the second layer may be a series of masked images for each of the regions of interest and an indicator for the type of feature that exists in the region of interest.

In another embodiment, the second layer may be broken up (or consolidated) into a different series of MLA; for example, the processing flow of the second layer may be arranged to divide the tasks of applying each mask to each region of interest and identifying the features of the region of interest into a single operation or further subdivide the processing into further operations.

A third layer of a multi-layered MLA may utilize the resulting masked regions of interest and identified features for each region to select an optimized OCR post-processing to extract the text from the region of interest. An exemplary optimized OCR post-processing for a section may include, e.g., a regular expression (e.g., "Name:", "DOB:", etc.), or a column-row pair(s) which contain key health information (e.g., Column 2, Row 2=Name; Column 2, Row 3=birth date; etc.). Further post processing of the OCR text may identify that regions of interest are related to one another. For example, a first region of interest may provide a series of gene variants while a second region of interest may provide the expression of those gene variants. In this example, there are a known number of genes, each having a plurality of possible variants, and a query to a molecular pathology service may be initiated to validate whether a recognized gene and variant combination is valid/known or if the combination is actually an unrecognized variant, an OCR introduced error, or if the unknown combination originated from the document. The MLA may detect that regions are related and assign a corresponding concept candidate using both of the regions of interest together. By utilizing relationships between regions of interest in the document, the MLA may provide a more robust classification and provide a more detailed error checking than an algorithm that analyzes portions of the document in isolation.

An unrecognized variant is one that has not been identified, sufficiently classified, or expertly-curated by the scientific community. Generally, reports include only known variants and publish updated documentation for any newly supported variants for each test/report offered. An output of the MLA from the third layer may be a collection of concept candidates or classifications for the document/patient. In another embodiment, the third layer may be broken up (or consolidated) into a different series of MLAs; for example, the processing flow of the third layer may be arranged to divide the tasks of text extraction, classification, and identifying relationships between regions of interest into a single operation or further subdivide the processing into further operations.

While the instant embodiments are described as including three layers with respective intermediate processing steps, it should be understood that each layer and the included intermediate processing steps may be reordered, combined, or skipped based on the layout of the training documents and configuration of the MLA. Therefore embodiments having fewer or extra layers may be realized without departing from the spirit of the disclosure.

Identifying regions of interest, features within the region of interest, or relationships between regions may be performed from the OCR text itself or processed from the image itself prior to OCR. For example, identifying a region of interest may be performed by identifying a border (e.g., black box) that encapsulates some segment of text. In some instances, a border may actually be identified using the negative space (i.e., the white space) around a text by observing that the white space is uniform all around a segment of text and creating a natural boundary. Other distinctions may be observed and utilized as well based on the MLA applied. For example, a table may be identified by observing two more intersecting lines. Similarly, lines segmenting the columns and rows of a table may be solid, dashed, or even extrapolated from the negative space between the words. Additionally or alternatively, OCR post-processing may recognize text which is presented in columns to combine the text in the correct order. Certain features may be identified based on the image of the text prior to OCR. For example, text in all capital letters may be identified by having more straight lines than typical text, bold text may be identified by having thicker letters than typical text, or italicized text may be identified by have angled lines more frequently than typical text. These features of text may be applied in determining regions of interest, related regions, or concept candidates from each region of interest. Furthermore, features of text may be identified by both image details (e.g., pixel density, pixel chroma, etc.) and text (e.g., the OCRed words themselves are shared between documents).

Returning to FIG. 1, once the pre-processing stage 120 has completed, the generated OCR output may be stored for later retrieval by the parser stage 130 of the intake pipeline 110. In an alternative embodiment, the preprocessing stage may check in with parser 130 to confirm availability and pass the OCR output to the parser stage directly. Due to the modular nature of the intake pipeline 110, each processing stage may process their respective data without regard for the specific OCR or pre-processing methods. A modular pipeline approach allows the pipeline to swap in and out the most appropriate OCR and pre-processing technologies to improve the results of the overall processing.

Sentence splitting is a function of NLP that may be incorporated to parse sentences into meaningful structures. Documents may arrive in either plaintext format (containing all text from the document) or in a structured OCR format (including the text as well as bounding boxes for every character, word, and sometimes paragraph if the model is capable of identifying paragraph regions). Conventional sentence splitting may be implemented by many readily available NLP applications, including, e.g., any of CoreNLP, Spacy, AllenNLP, or NLTK. The system may implement a plurality of NLP applications, and identifying a most appropriate tool for sentence splitting may be depend on the nature of the clinical documents at hand, since clinical documents have a large variety in document layouts and content. Each tool for sentence splitting has advantages for particular types of documents, expected sentence structures, etc. In particular, documents often have headers and footers with useful structured text data, but headers/footers may not be presented in a standard sentence format (e.g., document citation or quote) and may confound certain sentence splitters. Similarly, doctors may use clinical shorthand which conventional NLP tools are not trained to parse; for example, a doctor may write "pt dx luad 2017" to mean "the patient was diagnosed with lung adenocarcinoma in 2017."

These deficiencies in sentence splitting may be overcome by adding models before this stage to identify whether text is semi-structured data, well-formed text, clinical shorthand, uninformative headers/footers, etc. By creating methods for distinguishing between these types of text, the intake pipeline may use specific models to extract information from each type. For example, complex sentences may be broken down into simple sentences by looking for coordination constructs, adjectival clauses, evaluating parataxis, prepositional phrases, etc., by applying phrase-based or syntax-based machine translation approaches. For sentences which are are well-structured (e.g., following traditional grammar and prose), parse trees or deep semantic representations may be utilized. For sentences which are noisy (e.g, structured, but with unclear boundaries), a maximum entropy approach may be utilized. In texts which are very specialized in nature (e.g., medical texts, legal texts, etc.), a tokenization and document segmentation algorithm may be applied. By implementing sentence splitting, the processing pipeline may split the document into sentences for individual parsing.

Candidate extraction may be performed using one of above-referenced approaches. For example, one approach may include a symbolic approach that relies on the structure of the sentence. Relying on the structure means that the sentence may be passed into a dependency parser or constituency parser.

Constituency-based parse tree text analysis systems may incorporate a list of phrase types that are likely to occur in sentences containing medical concepts. A subset of phrase types from the improved list of concepts may include:

CC—Coordinating conjunction, (e.g., and, but);
CD—Cardinal number, (e.g., one, two, 1, 2);
DT—Determiner, (e.g., a, the);
EX—Existential clause, (e.g., there);
*FW—Foreign word, (e.g., absentia, nauseam, habeas);
IN—Preposition or subordinating conjunction, (e.g., although, because);
*JJ—Adjective, (e.g., wet, fast);
*JJR—Adjective, comparative, (e.g., -er);
*JJS—Adjective, superlative, (e.g., -est);
LS—List item marker, (e.g., numbering, bullets);
MD—Modal, (e.g., shall, will, might);
*NN—Noun, singular or mass, (e.g., cell, cancer);
*NNS—Noun, plural, (e.g., cells, fingers);
*NNP—Proper noun, singular, (e.g., California, London);
*NNPS—Proper noun, plural, (e.g., the Joneses, the Bushes);
PDT—Predeterminer, (e.g., both, a lot);
POS—Possessive ending, (e.g., 's);
PRP—Personal pronoun, (e.g., we, she);
PRP$—Possessive pronoun, (e.g., his, hers);
*RB—Adverb, (e.g., quite, then);
*RP—Particle, (e.g., not, to);
*SYM—Symbol, (e.g., @, &);
*UH—Interjection, (e.g., ah, oh);
*VB—Verb, base form, (e.g., run, inject);
*VBD—Verb, past tense, (e.g., ran, injected);
*VBZ—Verb, 3rd person singular present, (e.g., runs, injects);
WDT—Interrogative determiner, (e.g., what, which);
WP—Interrogative pronoun, (e.g., who, whom);
WP$—Possessive interrogative pronoun, (e.g., whose);
WRB—Interrogative adverb, (e.g., where, how); and
.—Period character.

While conventional implementations are not optimized for technical texts (i.e., medical texts), the conventional list of phrase types may be augmented to include additional phrase types to optimize sentence splitting for medical-based texts. Such additions have been indicated with an asterisk (*). Conventional implementations that involve constituency-based parse trees include Apache cTAKES (™), Stanford Parser, TensorFlow, and Charniak-Johnson.

Figure 3:
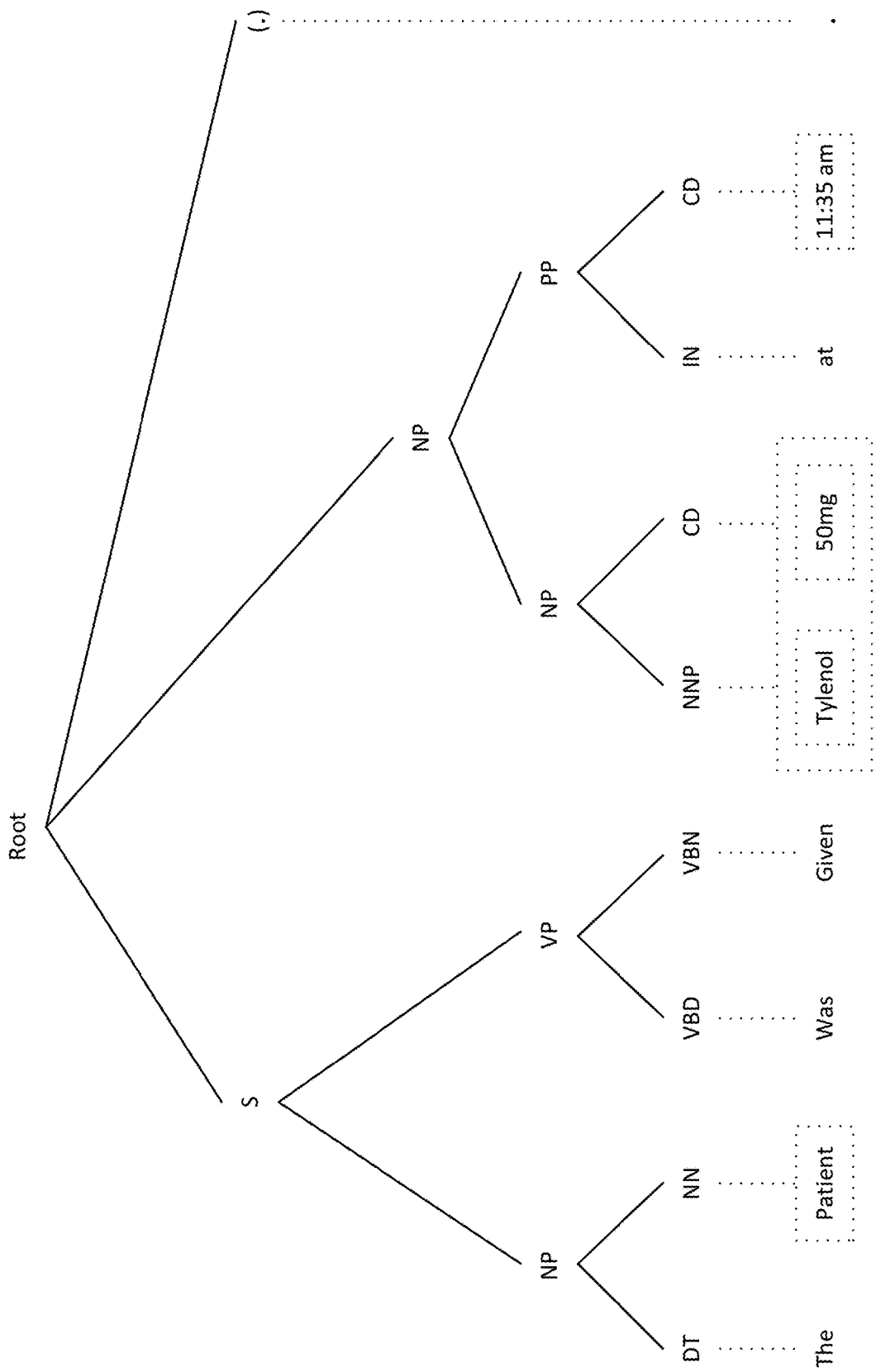
FIG. 3 is an exemplary constituency-based parse tree representation according to an embodiment.

Turning to FIG. 3, one example of a constituency-based parse tree is depicted. In that example, a constituency-based parse tree may receive a sentence "the patient was given tylenol 50 mg at 11:35 am." from which a parse tree may be generated. As depicted in the tree of FIG. 3, concepts may be identified (e.g., medical concepts) using different linguistic phrases and parts of speech. An example constituency parser then may generate: (ROOT (S (NP (DT The) (NN patient)) (VP (VBD was) (VP (VBN given) (NP (NP (NNP Tylenol) (CD 50 mg)) (PP (IN at) (NP (CD 11:35 am)))))) ( . . . ))).

In this example, phrase types: S, VP, NP, and PP markers are not in the above list. They represent the top-level sentence, verb phrase, noun phrase, and prepositional phrase, respectively. Furthermore, "patient", "Tylenol", "Tylenol 50 mg", "50 mg", and "11:35 am" may be included in a list of concept candidates (graphically represented as dotted lines around the words in the parse tree). Concept candidates may be determined by noting important phrase types (e.g., NP, CD, etc.) and may be further refined by comparing any associated text against a list of weighted words, whereby words which are weighted above a threshold weight may be presented as concept candidates. For example, the word "patient" may be flagged as a concept candidate, but due to its low weighting factor, may be removed from the candidate list.

In another embodiment, an MLA may be utilized to identify concept candidates. An exemplary MLA for identifying concept candidates includes a name entity recognition (NER) model. NERs may be implemented using conditional random fields, convolutional neural networks, attention based neural networks, long short term memory networks, or other neural models.

Language models may vary based upon the type of document being processed, (e.g., pathology reports, progress notes, and other EHR and EMR documents, etc.), to optimize the type of information which may be extracted from the documents. For example, a whole document classifier may be applied to a progress note (physician generated report of patient status on each checkup), pathology report, or other MR/EMIR documents to identify a patient's gender, cancer types, or other information that may require verification over one or more documents to provide reliable predictions. For a whole document classification, the text of the entire document may be evaluated before the document as a whole is classified (e.g., male/female, lung/breast cancer, date of birth, etc.). For other types of information, a sequence labeling classifier may be applied to a progress note, pathology report, or EMIR/MR documents to identify, for example, medications taken by a patient, therapies a patient may be undergoing, or other information which may be difficult to extract due to the extensive number of varying entries for each type of class. For a sequence labeling classification, each sentence, or combination of sentences in the document may be evaluated before the document is assigned another classification for identifying a class entry (e.g., a medication or therapy of the patient). The implementation details of an exemplary whole document classifier and sequence labeling classifier are discussed below.

In one aspect, a whole document classifier may rely on a training model that has been trained on thousands of medical documents found in EMRs and EHRs of patients. The training data may be provisioned with the parts of speech assigned to words and the true classification for each patient (e.g., male/female, age, ethnicity, etc.). A machine learning algorithm or a neural network may process the training data to generate a rule set or a trained neural network, respectively. In an exemplary rule set, a list of words with corresponding weights may be generated based upon the frequency they appear in text with proper classification vs text without the proper classification. For example, a rule set for determining if a document for a patient is to be classified according to gender may have a list of words including "male", "man", "he", "his", "testicular", "prostate", etc., which are weighted heavily towards identifying gender as male and a list of words including "female", "woman, "her", "she", "breast", "ovaries", "ovulation", "menstrual", etc., which are weighted heavily towards identifying gender as female.

The rule sets may include a vector of, for example, three hundred words and their respective weights, and each rule set may be applied over all words in a sentence to generate weights for every sentence. For example, a sentence "The patient was given prostate exam after he complained about having difficulty urinating in the mornings" may be given a high weight for gender as male because of words "prostate exam" and "he". After each word of each sentence is processed, each respective sentence may be assigned a sentence vector (e.g., 10% female, 90% male), then each sentence in a document may be processed to assign a document vector, and finally, each document in a patient's EMR or EHR may be processed to assign a patient vector.

At each level of granularity, the whole document classifier may be interrupted, for example, if a sufficient level of certainty has been reached or processing was intended to terminate at that level. For example, if a document has been determined to have a high incidence of accuracy because a table on page 3 of a document may always return the correct gender for the patient, then the algorithm may identify that high accuracy has been provided for the document based on the one sentence of that document and stop processing a gender classification at the sentence level vector for that patient. Furthermore, a patient level vector may not be generated if a document level vector has reached a certain threshold of certainty (e.g., 95%), or if, for example, only one document is being processed.

FIG. 4 provides a visual representation of word weightings for a sentence containing "The patient was given Tylenol 50 mg at 11:35 am." At the word level, "the", "was", "given", and "at", may be given low weights, "patient" and "11:35 am" may be given medium weights, and "Tylenol" and "50 mg" may be given high weights. As a result, the overall sentence may be classified with a high weight (e.g., 95%) that medication the patient has taken includes Tylenol 50 mg. For this example, because such a high confidence value is determined, the processing may not need to continue to evaluate other sentences in the document to determine that the patient did indeed take Tylenol 50 mg, but each sentence will be processed to determine if other concepts are identified (e.g., to identify gender, other medications, other treatments, or demographic information). In this example, even though only the medication concept is given a high weight, each of the identified concept candidates may be retained for the next stage of the intake pipeline for further processing; alternatively, those identified concept candidates may be dropped from the candidate list.

In some circumstances, a high level of confidence may not be available. For example, a patient who has undergone a gender reassignment surgery may have documents with a high level of confidence for one gender before surgery and a high confidence for another gender after surgery, or a document for a patient of a different gender may have been misfiled in the current patient's file. When a level of certainty lies below a threshold value (e.g., 90%), the whole document classifier may output the highest level vector calculated identifying, for example, a 60% confidence male and 40% confidence female. The output may also include one or more identifiers for which document, which section of which document, which sentence, or even which word from which the confidence values were calculated. In another embodiment, no prediction may be generated when the confidence value is below the threshold. In still other embodiments, documents which have contention in a prediction may be flagged, a true determination of classification may be obtained, and the documents and the true classification may be provided to a training engine which may retrain the rule set or neural network to further improve accuracy.

As discussed above, in another aspect, a sequence labeling classifier may be implemented. An MLA or neural network may be trained to generate a rule set identifying words and word sequences which are likely to identify concept candidates. Such concept candidates may include stand-alone words such as "patient," "age," or "gender," with a high stand-alone rating. It should be noted that these words may not be commonly coupled with other words in medical text but may still have some word couplings (e.g., under age). Other concept candidates may include words which are commonly linked to other words in a medical text. Words which commonly begin a multi-word concept include "breast" (e.g., breast cancer, breast reduction, breast augmentation, breast surgery) and "stage" (e.g., stage I cancer, stage II cancer, etc.). Other such words may include "high" (e.g., high blood pressure), "low" (e.g., low cholesterol), or "heart" (e.g., heart attack, heart failure). Words which commonly begin a multi-word phrase may feature a high beginning score and a medium stand-alone score. Intermediary words in a multi-word phrase (e.g., _____ cancer, _____ cell, _____ failure) are words which may have a high intermediary score and a medium stand-alone score). For example, each word in a sentence may be assigned a value for the likelihood that the word is a beginning of a multi-word phrase (e.g., a "B" value), an intermediary of a multi-word phrase (e.g. an "I" value), and a standalone word (e.g., an "O" value), and then each word or collection of words may be evaluated to identify clinical concepts.

Turning to FIG. 5, a sequence labeling classifier may provide a "BIO" score for each word, where a BIO score (10, 30, 60) would mean that the associated word is the first word in a multi-word phrase in about 10% of its occurrences in the training set, an intermediary word in a multi-word phrase in about 30% of its occurrences in the training set, and a stand-alone word in about 60% of its occurrences in the training set. For example, the word "the" almost always precedes another word and occasionally is an intermediary word of a multi-word phrase, so may be provided a BIO score of (90, 10, 0). "The" may also be considered an extraneous word, despite almost always preceding other words of importance, so it may be provided a BIO score of (0, 10, 90) to prevent processing, "patient" may be provided a BIO score of (5, 20, 75), and "was" may be provided a BIO score of (0, 0, 100). The sequence labeling model may begin processing the sentence at the first word, i.e., "the," and then note a high incidence of that word being the beginning value of a multi-word phrase (i.e., in the first incidence where BIO score is (90, 10, 0)), process the second word "patient" to note a high incidence of being an intermediary or stand-alone word, and process the third word "was" to note a high incidence of being a stand-alone word. By recognizing a potential beginning of a multi-word concept, a potential intermediary of a multi-word concept, and a distinct non-multi-word entry, the sequence labeling model may identify a first multi-word concept. Therefore the sequence labeling model may indicate "the patient" as a likely candidate concept for the multi-word label and "patient" as a likely candidate concept for the stand-alone word label.

Processing may continue word-by-word until another stand-alone word (B, I, or O labels) or multi-word (BIII . . . labels) are detected. In the example of FIG. 5, another multi-word phrase may be detected at "Tylenol 50 mg," and concepts "Tylenol" and "Tylenol 50 mg" may be generated. A final concept may be generated at "11:35 am."

A sequence labeling classifier may be able to identify labels with a higher accuracy than a parse tree by linking words together through their labels (e.g., BI, BII, BIII, etc.) to identify multi-word concepts (e.g., heart attack, stage IV cancer, medial tibial stress syndrome, etc.) as the totality of their concept rather than each of the words in multi-word concept.

The number of candidate concepts which may be extracted may be needlessly large. For example, in patient file with thousands of documents, a concept candidate for breast cancer may occur hundreds of times, a concept for lung cancer may occur tens of times, and a concept for liver cancer may only occur once. It may be useful to filter/rank the mentions of each concept candidate to reduce repetition in the following stages in the pipeline. For concept candidates which may be consolidated (e.g., mentions of breast cancer for diagnosis) the concept candidate may be reduced to a single concept with a count field in the hundreds. Furthermore, if concept candidates are competing for the same field, the concept candidate may be coupled with a reliability index based upon the frequency of the concept candidate occurring in relationship to the others (e.g., 200 mentions of breast cancer, 13 mentions of lung cancer, and 1 mention of liver cancer may be processed to a 200/214 reliability index that the patient has breast cancer). The highest ranked competing concept candidate may be preserved along with a reliability index, or a consolidated report of the most frequent competing concept candidates may be preserved along with their count values and/or reliability index.

Using any of the above methods, candidate extraction generates a plurality of candidate concepts which may be evaluated in the following stage for entity linking.

Returning to FIG. 1, the entity linking pipeline stage 140 receives/retrieves the candidate phrases as a list and may process each candidate to identify any links between the phrases and known entities (e.g., the enumerated list of medical drugs discussed above). Entity linking is the task of determining whether a candidate concept (i.e., phrase) is a relevant clinical concept. Relevancy may be determined by the presence of the candidate concept in any medical dictionary or the universal dictionary described above. Relevancy may also be determined based on proximity to a concept candidate hit. For example, a time "11:35 am" may not result in a hit in any dictionary as a medical concept. However, certain medical concepts, such as medications, may fall within an abstraction category such as treatment. A treatment may have fields such as treatment type (i.e., the medicine) and date and time of treatment (i.e., 11:35 am). By considering proximity to other concept candidates, key information may be retained even if the concept may not exist in the database. The retained candidate concept may not be classified as a linked entity, but may be associated with the linked entity for abstraction purposes.

Within the entity linking pipeline stage 140, the list of concept candidates generated in the previous pipeline stage may be provided to a dictionary lookup for matches. Conventional dictionary lookup tools may include Elasticsearch, Solr, Algolia, or Sphinx. In one aspect, a direct dictionary lookup may not always result in a database hit (i.e., the candidate is in the database) because of typographical errors, OCR errors, shorthand, or other confounding factors. In those situations, candidates which are not an exact match may still be found in the database by applying fuzzy matching logic. For example, the entity linking pipeline stage 140 may expect to find matches for "Tylnol" and "Tylnol 50 mg" because exemplary queries allow for "fuzzy matching," which will correct potential typographical errors or OCR errors that occur in "Tylenol."

Fuzzy matching may be implemented by an approximate string matching algorithm. For example, in conventional string matching, a string must exactly match, character for character, with a reference string in order to yield a positive match result. In fuzzy string matching a string is still matched character by character; however, for each mismatch in character, operations may be performed to elicit a match. For example, a mismatching character may be deleted, and the next character considered for a hit, which would account for having an extraneous character in a word, a character may be inserted at the mismatching character to provide a match to allow a match to occur even if a character was omitted, a character may be substituted at the mismatching character to allow a match even if the wrong character was inserted, or a character may be transposed at the mismatching character. For each mismatch operation that is performed, a counter may increment to track the number of errors allowed. In an embodiment, the number of errors may be capped to restrict the flexibility of the fuzzy searching algorithm (i.e., only three mismatch corrections allowed before no match may be identified). Other embodiments may adjust the threshold based upon the length of the word to allow longer words more mismatches than shorter words. For example, if a three letter word is allowed three mismatch operations, then a fuzzy string matching algorithm may generate matches for thousands of concepts from 1-6 characters.

Fuzzy matching is structured around the text concepts included in the above enumerated list or the UMLS, including metadata fields CUI (the UMLS unique ID) and AUI (dictionary-specific unique ID), so that an exhaustive search may be performed for all medical concepts. The dictionary search engine may also return metadata about the specific entry detected (e.g. universal ID assigned in the above enumerated list or the UMLS), which is useful for understanding Tylenol as a medical concept and not just the correct spelling of a drug. At the end of text normalization, some of the extracted candidates may have zero matches but others may have many matches. For example, there are many versions of Tylenol throughout the UMLS database because of the number of dictionaries represented therein. Fortunately, the CUI (the UMLS uuid) provides a generalization to join similar concepts, which reduces the number of matches from one for each potential database to the number of unique CUIs represented. Not all concepts can be simplified so succinctly, though. For example, "Tylenol" is a different concept than "Tylenol 50 mg", which is a dosage-specific version of "Tylenol". Any ambiguation from "Tylenol 50 mg" to "Tylenol" would effectively constitute a loss of information.

Fuzzy matching may also apply on a word-by-word basis rather than a letter-by-letter basis. For example, a concept candidate may include the phrase "needle biopsy." An entity matching search may identify entities linked to, for example an exact match ("needle biopsy"), a reordered match ("biopsy needle"), or phrase matches of "needle aspiration biopsy of lung" or "breast needle biopsy." Such entity matches may be derived using the same fuzzy matching operations above (deletion, insertion, transcription, etc), but on the whole word rather than each individual character. Furthermore, in still another embodiment, both fuzzy matching on a character by character basis and word by word basis may be applied concurrently to generate entity matches. When operating as an ontology-directed system that specializes in abstracting patient from fields from a particular ontology, dictionary lookups may be relaxed to allow for wider inferences. This may include allowing more wildcards into the phrase search or other adjustments to allow for broader lookups. When operating as a system having aspects that are ontology agnostic for performing recognition across multi-discipline medical records, dictionary lookups may be more strict, allowing less flexibility or wild characters for matching.

Certain features, such as the TNM Classification of Malignant Tumors (TNM) is a globally recognized standard for classifying the extent of spread of cancer, must be preempted from fuzzy matching. TNM is a notation system that describes the stage of a cancer, which originates from a solid tumor, using alphanumeric codes: T describes the size of the original (primary) tumor and whether it has invaded nearby tissue; N describes nearby (regional) lymph nodes that are involved; and M describes distant metastasis (spread of cancer from one part of the body to another). For example, T may be designated a value to estimate size or direct extent of the primary tumor (Tx: tumor cannot be assessed, Tis: carcinoma in situ, T0: no evidence of tumor, T1, T2, T3, T4: size and/or extension of the primary tumor), N may be designated based upon the degree of spread to regional lymph nodes (Nx: lymph nodes cannot be assessed, N0: no regional lymph nodes metastasis, N1: regional lymph node metastasis present; at some sites, tumor spread to closest or small number of regional lymph nodes, N2: tumor spread to an extent between N1 and N3 (N2 is not used at all sites), N3: tumor spread to more distant or numerous regional lymph nodes (N3 is not used at all sites), and M may be designated based upon the presence of distant metastasis (M0: no distant metastasis, M1: metastasis to distant organs (beyond regional lymph nodes)). Exemplary TNM codes may be "pT1 pN0 M0" or "pT4 pN2 M1". Due to the importance of the TNM codes being parsed precisely as they appear to maintain the TNM values, fuzzy matching may be disabled for stop words relating to TNM values, for example, "t0", "T1a", "t3", so that fuzzy matching does not change a "t1" into a "t2" to match a database Entity. NLP may be combined with restricted fuzzy matching in certain embodiments to correct OCR errors related to TNM codes. For example, a NLP model may detect that TNM is being referenced by detecting the presence of a T, N, and M code; however, classification may fail due to an OCR of "pT0" with "pTo", by allowing a restricted fuzzy matching of only similar characters (e.g., an "o" for an "0"), TNM codes may be maintained while still correcting for errors.

Due to the large volume of concept candidates that may exist from the previous pipeline stage, merely searching for a match and terminating the search upon finding a single match may provide a substantial benefit in reducing the processing time spent crawling the relevant databases/dictionaries. However, the best matches may not be the first matches, and if there are multiple matches within a group (e.g., synonyms which are off by a single word to the concept candidate), it may be necessary to pick the match which has the lowest fuzzy "score" (i.e., the value that counts the number of errors corrected to generate the fuzzy match). If there are still ties (e.g., there are two matches of equal fuzzy "score"), then the tied matches may be sorted based on length of characters or length of words (e.g., shorter matches with less words/characters score higher than longer matches with more words/characters). Any unresolved matches may then be selected randomly or according to a first-in, first-out FIFO queue of matches, such that the first match is selected.

Templates, Fuzzy Text Matching & Regular Expressions:

Many reports within EMRs and EHR are provided in consistent formatting across institutions for periods of time (e.g., patient intakes may share the same form for a period of time until the next revision). Relying on this consistency, the system may consider a case where a hospital system prints its pathology reports using the same template and had a different template for any documents that were created before Jan. 1, 2001. If Pathology Reports from this hospital system are identified as frequent documents received in EMR and EHR, optimizations may be applied to processing to create methods for extracting information from known locations within the shared templates of each respective form. An exemplary method (e.g., the method described above) may also include multiple parts, as follows:

Document classification: The system may generate an image or text classification model to: determine whether a given document belongs to one of the templates that may be extracted from, assign the document an identifier for linking the document to the template, use the identifier to look up the classification model optimized for the document, and classify the document. Exemplary template-based approaches and tabular approaches are discussed above.

Regular Expressions: The system may identify anchor strings regularly occurring in text that identify where key health information may reside. For example, the system may recognize that "DOB" is a string to search for dates of birth and "Pathological Diagnosis" may be a header to a section that provides concepts for linking to a pathological diagnosis.

Fuzzy Text Matching: As discussed above, the system may apply a fuzzy search algorithm to a regular expression in order to allow the application of regular expressions to words which have OCR errors, typographical errors, or are otherwise confounded.

Templates: Once a document has been classified, and regions of text may be determined in advance, an image classification model may leverage the predetermined region locations to identify those same regions within a document image to extract key health information (clinical concepts). For example, document headers may often be visually structured for presenting information to the reader, and that known visual structuring may contain useful demographic information. By identifying a document header, processing may include rotating/skewing the image to line up the template, removing image irregularities, OCR of the text, and applying regular expressions to extract any information from the standardized format. Any concepts extracted from the template may be provided to the entity linking pipeline 140 and may be processed to identify any respective matching concepts for linking.

Returning to FIG. 1, in another embodiment, entity normalization (e.g., at step 150) may be applied to determine which of the entity linked concepts of the previous stage are relevant to abstraction and, if they are relevant, which encoding schema may be applied to encapsulate the abstraction completely. For example, "Tylenol" and "Tylenol 50 mg" may match in the dictionary from UMLS with a concept for "amphetamine". It may be necessary to explore the relationships between the identified concept from the UMLS dictionary and any other concepts of related dictionaries or the above universal dictionary. Though visualization is not required, these relationships may be visualized through a graph-based logic for following links between concepts that each specific integrated dictionary may provide.

Figure 6:
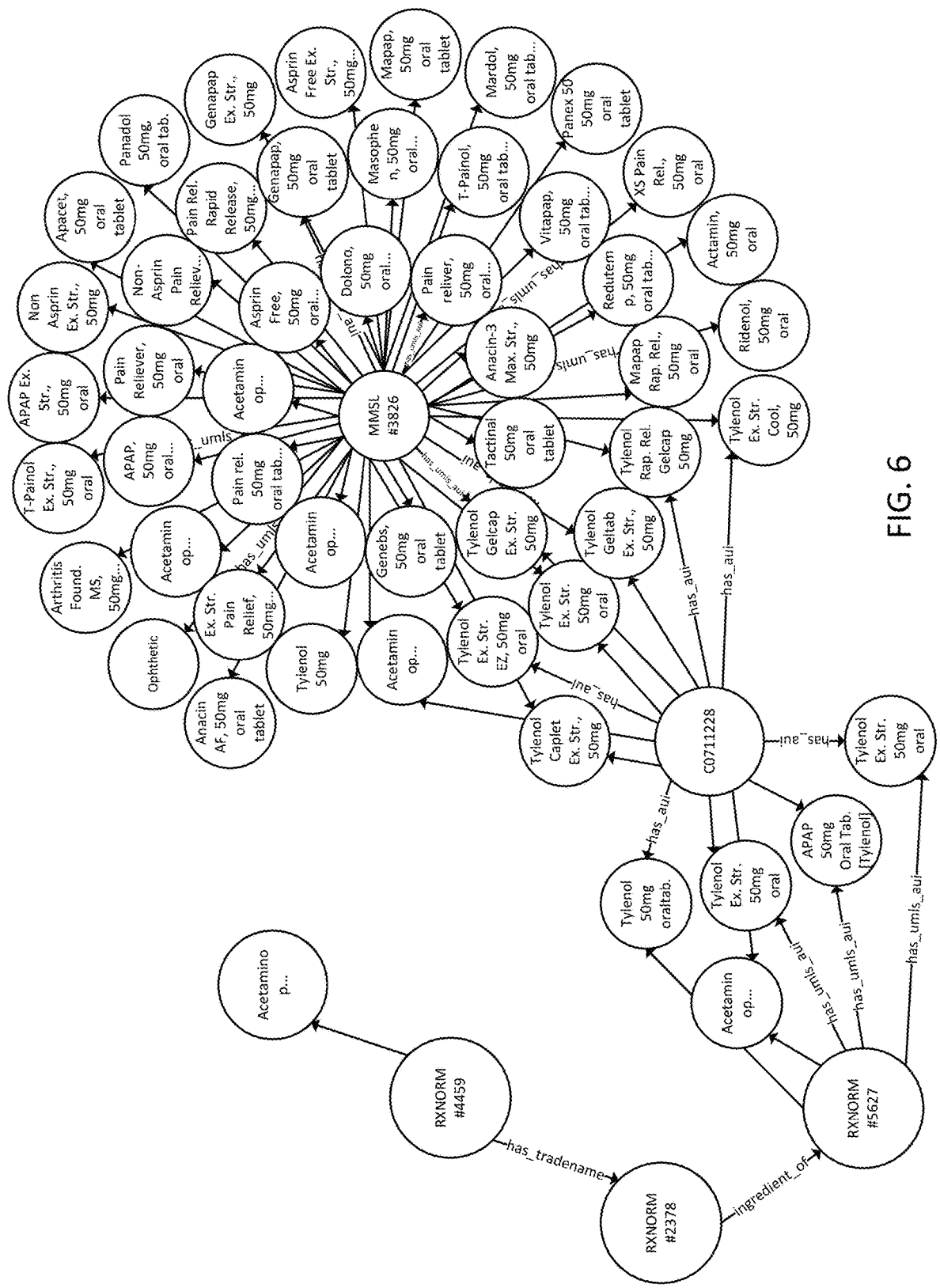
FIG. 6 is an exemplary ontological graph database for viewing links between different dictionaries.

FIG. 6 is an exemplary ontological graph database for viewing links between different dictionaries (databases of concepts) that may be interlinked through a universal dictionary lookup in order to carry out the normalizing stage 150 in FIG. 1. Conventional ontological graph databases may include GraphT, Neo4j, ArangoDB, Orient, Titan, or Flockdb. The following references to dictionaries and databases are for illustrative purposes only and may not reflect accurately the concepts/synonyms, entities, or links represented therein. Links between two concepts may represent specific known relationships between those two concepts. For example, "Tylenol" may be linked to "acetaminophen" by a "trade name" marker, and may be linked to "Tylenol 50 mg" by a "dosage of" marker. There may also be markers to identify taxonomic "is a" relationships between concepts. "Is a" markers provide relationships between over some clinical dictionaries (e.g., SNOMEDCT_US, Campbell W S, Pederson J, etc.) to establish relationships between each database with the others. For example, we can follow "is a" relationships from "Tylenol", "Tylenol 50 mg", or "acetaminophen" to the concept for a generic drug. Such a relationship may not be available for another concept, for example, a match to the dictionary for UMLS to "the patient" or "patient" may not have a relationship to a medication dictionary due to the conceptually distinct natures of each entity. Relationships may be found between drugs that have the same ingredients or are used to treat the same illnesses.

Other relationships between concepts may also be represented. For example, treatments in a treatment dictionary may be related to other treatments of a separate treatment database through relationships describing the drugs administered or the illness treated. Entities (e.g., MMSL #3826, C0711228, RXNORM # . . . , etc) are each linked to their respective synonyms, (e.g., Tylenol 50 mg, Acetaminophen, Mapap, Ofirmev, etc.). Links between concepts (i.e., synonyms), may be explored to effectively normalize any matched candidate concept to an RXNORM entity.

Returning to FIG. 6, the concept candidate "Tylenol 50 mg" may have a hit in the National Library of Medicine Database MMSL. In the preceding stage of the pipeline, "Tylenol 50 mg" may have been linked to the Entity MMSL #3826 as an identifier for the "Tylenol 50 mg" concept in MMSL. The linked Entity, MMSL #3826, may reside in a database which is not a defined database of authority, or, for document classification purposes, MMSL #3826 may not provide a requisite degree of certainty or provide a substantial reference point needed for document/patient classification. Through entity normalization, it may be necessary to explore links to MMSL #3826 until a reference entity of sufficient quality is identified. For example, the RXNORM database may be the preferred authority for identifying a prescription when classifying prescriptions a patient has taken because it provides the most specific references to drugs which are approved by the U.S. Food and Drug Administration (FDA).

Other authorities may be selected as the normalization authority based upon any number of criteria. The exact string/phrase "Tylenol 50 mg" may not have a concept/entity match to the RXNORM database and the applied fuzzy matching may not generate a match with a high degree of certainty. By exploring the links from MMSL #3826, it may be that concept "Tylenol Caplet Extra Strength, 50 mg" is a synonym to "Tylenol 50 mg" in the MMSL database. Furthermore, concept "Tylenol Caplet Extra Strength, 50 mg" may also be linked to Entity C0711228 of the UMLS database. By exploring the synonyms to "Tylenol 50 mg" through Entity MMSL #3826, the concept candidate may be linked to the UMLS Entity C0711228. However, the UMLS Entity C0711228 is not the preferred authority for linking prescriptions, so further normalization steps may be taken to link to the RXNORM database. Entity C0711228 may have synonym "Tylenol 50 MG Oral Tablet" which is also linked to RXNORM #5627. RXNORM #5627 may be a normalization endpoint (i.e., once RXNORM #5627 has been identified, normalization may conclude); however, RXNORM #5627 may also represent the Tylenol specific brand name rather than the generic drug name. A degree of specificity may be placed for each source of authority (i.e., normalization authority) identifying criteria which may be desired for any normalized entity. For example, a medication may need to provide both a brand drug name and a generic drug name. Links in the RXNORM database may be explored to identify the Entity for the generic drug version of Tylenol. For example, RXNORM #5627 may have an "ingredient of" link to RXNORM #2378 which has a "has tradename" link to RXNORM #4459 with concept acetaminophen. RXNORM #4459 is the Entity within the RXNORM database which represents the generic drug for Tylenol 50 mg and is selected as the normalized Entity for identifying a prescription in the classification of prescriptions a patient has taken. In this aspect, normalization may first identify an Entity in the dictionary of authority (as defined above) and may further normalize within the dictionary of authority to a degree of specificity before concluding normalization.

For each field of medical data that is abstracted in the intake pipeline, reasonable reference points for normalization may be identified (e.g., RXNORM for medications, SnoMed for cancers) and which types of relational links may be traversed from matched concepts in the fields of medical data. As described above, medical data may include fields of patient demographics (e.g., patient name, date of birth, gender, ethnicity, date of death, address, smoking status, diagnosis dates, personal medical history, family medical history, etc.), clinical diagnoses (e.g., date of initial diagnosis, date of metastatic diagnosis, cancer staging, tumor characterization, tissue of origin, etc.), treatments and outcomes (e.g., therapy groups, medications, surgeries, radiotherapy, imaging, adverse effects, associated outcomes, and corresponding dates, etc.), and Genetic Testing and Labs (e.g. genetic testing, performance scores, lab tests, pathology results, prognostic indicators, and corresponding dates, etc.). Each of the fields (e.g., address, cancer staging, medications, genetic testing, etc.) may also have a plurality of subfields. For example, address may have subfields for type of use (e.g., personal, business), street, city, state, zip, country, and a start or end date (i.e., date that residency at the address begins or expires). Genetic testing may have subfields for the date of genetic testing, testing provider used, test method (e.g., genetic sequencing method, gene panel), gene results (e.g., included genes, variants, expressions, etc.), tumor mutational burden, and microsatellite instability. For medications, links as described above, including "has tradename" and "dosage of" relationships from any entity links may be traversed determine if there is a relevant drug related to the candidate concept.

In another embodiment, a linked Entity may be received from the entity linking stage of the intake pipeline. A query may be generated to search over an ontological graph database having relationships including meta-synonymous links, synonymous relationships between links, and other relationships. For example, a linked entity may resolve to Ductal Carcinoma In Situ (DCIS) in the SnoMed dictionary. SnoMed may be the preferred authority for cancers due to degree of comprehension and detailed concepts included in the dictionary, expert opinion identifies SnoMed as the best dictionary, or because SnoMed has the most comprehensive relationships between other dictionaries, is well established, and meets requirements set forth by the institutions managing the EMR/WHR. A desired degree of specificity may have selection criteria for normalized endpoints. For example, the selection criteria of a cancer type may include an Entity which identifies 1) the cancer site (i.e., where the cancer is located in the patient) and 2) the cancer type. An entity identifying DCIS may be limited to identifying the cancer type, but may not satisfy the cancer site selection criteria and SnoMed may be searched to identify a normalized Entity which satisfies both criteria.

Normalizing DCIS may include navigating "is a" relationship links within the SnoMed database until an Entity is reached which identifies the cancer site as breast. For example, DCIS may be a tier three entity which "is a" specific type of cancer under "breast cancer." Breast cancer may be a tier two entity which "is a" specific type of cancer under the root "cancer." Breast cancer may have a "has finding site" relationship to breast, which satisfies the selection criteria for identifying the cancer site (i.e., breast) and the cancer type (i.e., breast cancer). However, to prevent loss of information, both the DCIS Entity and Breast Cancer Entity may be retained for the normalized Entity to aide in Entity Structuring described below. In SnoMed, relationships between cancers are structured such that there is a finite number of jumps that "is a" links may traverse. Upon each traversal, an "is a" link may either result in a leaf node (traversed down), a terminal node (cancer with no further classification), or to the root (i.e., cancer). Traversal may stop at the first "is a" link which is encoded as a terminal node (e.g., based on the tier as described above, based off a relationship that exists in the node as described above, or that is predetermined as a terminal node). Other relationships which may identify terminal nodes include, for example, in a medicine dictionary, Term Types "Ingredient" or "Preferred term" (e.g., TTY: GN for Generic Drug Name and TY:BD/BN/FBN for Branded Drug/Name or Foreign Brand Name, etc.), or the degree of specificity may be based off of relationships (e.g., "is a generic", "is a brand name").

Normalization queries are constructed to prevent out of bound searches, surprious results, infinite searches, and other logic that prevents a query from completing. A representative normalization query of a medication may include:

MATCH p=(start:DICT {code: "DICT#AUI" })-[:has_tradename|
  tradename_of*0 . . . 3]-(end:DICT)-[:has_umls_aui]→
  (aui2)←[:has_aui]-(descendant_cui)
RETURN DISTINCT descendant_cui.cui AS match_cui,
  length(p) AS graph_distance This query may return CUI's related to concepts which are linked to ingredients identified in the medications terminal node list by up to 3 trade names or generic names. In one aspect, a limit on the number of links which may be traversed and included in the query results may be included to reduce computational constraints (e.g., processor and memory reservations). Queries may be optimized to provide both generic and trade name normalization endpoints, for example, by not specifying or restricting the directionality of the [:has_tradename|tradename_of] portion of the query. Alternatively, queries may be directionally limited to only traverse [:has_tradename|tradename_of] in a specified direction to limit the results which are generated as desired. A terminal node entry for an ingredient to be encoded to in the medications valueset and may be encoded by including each respective code's dictionary (DICT above) and AUI into the query so that when a new entity is traversed, the AUI may be referenced with the list of terminal nodes.

A representative normalization query for a cancer type may include:

MATCH p=(cui:umls_cui)-[:has_aui]→(aui:umls_aui)←
  [has_umls_aui]-(descendant:DICT)-[:isa*0 . . . ]→
  (:DICT {{code: "DICT#AUI" }})
RETURN DISTINCT cui.cui AS match_cui, length(p)−2
  AS graph_distance This query may return CUI's related to concepts which are linked as "is a" descendants of a given code (i.e., node). A terminal node entry for a cancer type may be encoded in the cancer valueset and may be encoded as a primary diagnosis by including each representative code's dictionary (DICT above) and AUI into the query so that when a new entity is traversed, the AUI may be referenced with the list of terminal nodes. For cancer type queries, a return value may include the graph_distance of the path, which provides a qualifier for how many "is a" nodes are in the path between the descendant and the queried code. After processing queries for each node in the primary diagnosis valueset, there may exist many descendants that point to multiple parents. The resulting query response of potential matches may be further curated according to the following logic:

If a descendant D is generated by two ancestors A and B, but A and B are not descendants of each other, then keep the mapping of D to both A and B; OR If a descendant D is generated by two ancestors A and B, but A is also a descendant of B, then discard the mapping of D to B (because A is a nearer ancestor).

In another embodiment, a concept candidate may be explored by more than one query relating to the concept. For example, a concept candidate may be explored/followed until a concept with a related structure (as described in FIG. 2) is linked/normalized, then each of the associated fields are queried in turn (Entity structuring is disclosed in more detail, below).

An aspect of query generation may include tailoring queries to avoid spurious searches. For example, by recognizing directional relationships which preserve the integrity of the source node, queries which prevent erroneous destination nodes from being reached are preferred. For example, normalizing the Brand Name Entity for Tylenol may include traversing the "ingredient of" relationship that Tylenol has. In one direction, drugs for which Tylenol is considered an ingredient of may be safely explored. However, in the other direction, the ingredients of Tylenol may be explored. An ingredient which is shared between Tylenol and another drug may be linked by, for example, magnesium stearate which is shared between Tylenol and Advil. A generic drug ibuprofen may then result from an unbounded query which does not restrict the traversal of "ingredient of" fields to prevent spurious drug hopping.

It may be advantageous to precalculate the results from frequent query searches and cache the query results for speed. Caching precomputed queries represent a tradeoff for the flexibility of results with the speed at which they may be generated. Caches may include a node hop count value that is used to resolve ties for least number of hops. Caching may be performed at the Entity Link stage and the Entity Normalization Stage. In a simplified representation, an Entity Linking Cache may include fields such as: Name of Concept Candidate, Dictionary Candidate Located In, and CUID. It may further be advantageous to identify a structure category and corresponding fields based from the identified CUID. Normalization may be directed to generate results which relate to the fields of the structure category identified. In another simplified representation, an Entity Normalization Cache may include fields such as: CUID, Medical Concept Structure, and normalized response for concept (Normalized CUID). Additional fields for either table may include: graph distance (i.e., number of hops), preferred dictionary CUID, pre-defined entries (e.g., names, regions, categories), inferred structure entries (e.g., diagnosis site, generic drug name), language of text, match type (e.g., exact, exact but letter case mismatch, fuzzy matched, etc.), text type (i.e., TTY, described above), or other fields.

Normalized Entities may be further normalized to reduce known variance in results. For example, in a cancer type normalization, there may be numerous normalization endpoints which reference breast cancer in one form or another that match the selection criteria of the normalization algorithm. A post-processing step to the normalization may be applied which identifies, for example, when a cancer site is designated as breast, and adjusts the final result such that all entries with a breast cancer site share the same cancer site code and same spelling "breast". Other normalized results may include each main cancer site (brain, lung, liver, ovary, bone marrow, etc.), a predetermined catch-all for unknown sites, or known codes which are irrelevant to the normalization results and may be filtered.

Returning to FIG. 1, the Entity structuring pipeline 160 compiles each of the normalized concepts identified in the previous stage. However, given thousands of pages of documentation within an EMIR/MR for a patient, the number of normalized entities that may be identified and resolved during processing may number in the hundreds of thousands. The abstraction process as described above with reference to FIG. 1, may display information about a normalized concept by providing various identified and populated fields. For example, with reference to the sentence "The patient was given Tylenol 50 mg at 10:35 am," the entity structuring pipeline 160 may encode the following fields:

Text: The entirety of the text (i.e., "The patient was given Tylenol 50 mg at 10:35 am.").

Medication: Identifying any medication mentioned in the text (i.e., Tylenol). Medications may be brand name or generic name. This field does not include information about the dosage or method of administration.

Active Ingredient: Identifying the active ingredients (i.e., acetaminophen) of the medication mentioned using a list such as a search table linking drug names to their active ingredients.

Dosage & Dosage Units: The dosage (i.e., 50 mg) associated with the medication mentioned. In the above example, identifying that the dosage as 50 mg is fairly straightforward by reading the sentence, but clinical data is often printed in tables with a variety of structures that are not easy to infer. As such, normalizing the dosage and dosage units by separating value 50 into the dosage field and string "mg" or by selecting a known value entry for the milligram units within a list may be preferable.

Document & Page: The document and page where the text is found (i.e., Progress Note 01_01_01.pdf and page 3).

UMLS_CUI: The CUI field (i.e., C0711228) of the UMLS entry corresponding to the medication. The UMLS is a list of medical concepts and the UMLS_CUI refers to the CUI field, which is UMLS' universal identifier. UMLS is comprised of a number of independently maintained clinical dictionaries and ontologies (e.g. those for cancer diagnosis & treatment, dentistry, veterinarian medicine, etc.). That is, the CUIs are universal to UMLS, and there is only one CUI for Tylenol across all of its constituent dictionaries that enables UMLS to unite all of these disparate sources.

UMLS_AUI: The AUI field (i.e., RXNORM #4459) is the dictionary-specific identifying code of the UMLS. Where the CUI is universal, and has the same entry across all included sources, the AUI for Tylenol will have different AUIs for each dictionary that it has an entry in.

Various fields, e.g., UMLS_CUI, UMLS_AUI, Medication, and Active Ingredient may each be determined through the entity normalization process by exploring the links to each of the Entities. The other fields, e.g., dosage, dosage units, date/time administered, document, and page may not be determined through the normalization process. Instead, these other fields are provided to a Relational Extraction MLA for extracting this information from the surrounding context or document information (e.g., name, number of pages, etc). For example, a document named Progress Note 01_01_01 may be presumed to have a date of Jan. 1, 2001. Other concept candidates from the document may be referenced to validate the date/time or select the date absent any other validating/corroborating information. For example, the time 11:35 am may have been provided as a concept candidate spatially near the "Tylenol 50 mg" concept candidate. The Relational Extraction MLA may then identify 11:35 am as the time the medication was administered based on the concept candidate time being the next concept candidate in the list, a spatial proximity of the concept candidate, a new application of NLP to the OCRed text string, or any combination thereof. Additionally, a page number may be identified, for example, in a document that has 5 pages by referencing the page number by performing an OCR of text at the bottom of the page or may be extrapolated by counting the number of pages before the page the concept candidate was extracted from. Once each field of the medical data is identified through either the normalization process or the structuring process and the relational extraction MLA, the patient/document may be ready to be classified according to each normalized and structured entity.

Normalization of linked entities may be provided across the entire feature set detailed herein. The following examples are provided for illustrative purposes.

In one example, a patient record may contain the sentence: "Patient reports feeling queasy, unusually tired, and bleeding in the mouth since being placed on amithopterin, but says that these side effects are mild in severity." Abstraction may include generating the following results:

| Text | Concept Type | Matched Concept | Canonical Concept | UMLS CUI | Concept Name |
|---|---|---|---|---|---|
| feeling queasy | Adverse Event | MDR#10037730 | MDR#10028813 | C0027497 | Nausea |
| unusually tired | Adverse Event | MDR#10043890 | MDR#10016256 | C0015672 | Fatigue |
| bleeding in the mouth | Adverse Event | CHV#0000008993 | MDR#10030980 | C0029163 | Oral Hemorrhage |
| amithopterin | Medication | SNOMEDCT_US#387381009 | RXNORM#6851 | C0025677 | Methotrexate |

A text match for feeling queasy may be a hit to a first adverse reaction concept. However, a concept matching a colloquial phrase may not satisfy a predetermined degree of specificity for adverse reactions. For example, the concept matching the phrase feeling queasy may be a child concept of nausea, a formal medical term that encompasses the colloquial phrase feeling queasy. In such an example, the parent concept nausea may satisfy the predetermined degree of specificity for adverse reactions because it resides at a higher level of the adverse reaction ontology tree or contains metadata identifying it as a formal medical term. Such a predetermined degree of specificity may be based on the number of branches from the root of the tree, or a metadata of the ontology indicating a level of specificity such as a status as parent node, a node having formality, a node with no other parents, or a node defining a set of characteristics of the child nodes. In this particular case, the preferred concept Nausea may also be a technical term for the condition and may the parent concept of numerous synonymous, less technical or more ambiguous terms, including: "feeling queasy", "feeling sick", "feeling bilious". Each child term may be assigned the same parent entity to ensure cohesive abstraction across all patient records.

For many preferred concepts it may be advantageous to encode one or more child phrases to a resource for maintaining standardized parent concepts. In some embodiments, standardized concepts may have many synonyms in another vocabulary and the encompassing vocabulary may be selected as the preferred vocabulary due to having the most complete coverage for the concepts relating to the abstraction purpose. For example, it may be advantageous to assign RXNORM as the preferred vocabulary for medications when the abstraction purpose has records of cancer patients because it has the broadest coverage for the concept of medications most relevant to the cancer domain.

In another example, a text match for unusually tired may be a hit to a first adverse reaction concept. However, a concept matching a colloquial phrase may not satisfy a predetermined degree of specificity for adverse reactions. For example, the concept matching the phrase unusually tired may be a child concept of fatigue, a formal medical term that encompasses the colloquial phrase unusually tired. In such an example, the parent concept fatigue may satisfy the predetermined degree of specificity for adverse reactions because it resides at a higher level of the adverse reaction ontology tree or contains metadata identifying it as a formal medical term.

In some instances, a first matching phrase may not reside in a source of authority. For example, "bleeding in the mouth" may lead to a hit because an AUI exists in the consumer health vocabulary (CHV), which lists colloquial and informal terminology. However, entity CHV #8893 lies in an ontology that is not the preferred ontology for adverse reactions (such as ontology metadata description and registry (MDR)) mapped to technical terminology through UMLS CUIs. In this case, "Oral Hemorrhage" may be the technical term linked to the MDR ontology but may not appear in the CHV ontology.

In other instances, patient records may reference older terms for medications which are no longer in use. A medication ontology may include mappings from obsolete namings to current medication or drug names. In one example, "Amithopterin" is an obsolete term which has been deprecated in favor of a more current "Methotrexate".

In one example, a patient record may contain the sentence, "The patient reports that he is a non-smoker and does not drink alcohol." Abstraction may include generating the following result:

| Text | Concept Type | Matched Concept | Canonical Concept | UMLS CUI | Concept Name |
| --- | --- | --- | --- | --- | --- |
| non-smoker | Smoking Status | NCI#C65108 | SNOMEDCT_US#266919005 | C0425293 | Never Smoker |

A phrase match for "Non-smoker" may receive a hit in an NCI ontology; however, without qualification may better be represented by the term "Never Smoker", which represents a person with no smoking history. An abstraction specialist may have created a look-up table with relational linking from an undesired source to a source of authority. A phrase match to the table may then be automatically assigned the appropriate entity.

In one example, a patient record may contain the sentence, "Recommend following up with interstitial brachytherapy to the lumpectomy site." Abstraction may include generating the following results:

| Text | Concept Type | Matched Concept | Canonical Concept | UMLS CUI | Concept Name |
| --- | --- | --- | --- | --- | --- |
| interstitial brachytherapy | Radiotherapy Modality | SNOMEDCT_US#113120007 | SNOMEDCT_US#399315003 | C1881237 | Brachytherapy |
| lumpectomy | Surgical Procedure | NCI#C15755 | SNOMEDCT_US#64368001 | C0851238 | Lumpectomy of breast (procedure) |

A phrase match for "interstitial brachytherapy" may be one of many child concepts of "brachytherapy". Given the sheer number of alternatives for representing each modality of radiotherapy, each child concept may be assigned a parent concept that is not a strict parent in the ontology, that is, the entity corresponding to C1881237 may not be a parent entity in the ontology, but a mapping for all associated terms may be manually or automatically curated and assigned the singular parent in the look-up table. In such a manner, an appropriate parent concept may be substituted to ensure that all terms for the same concept are assigned a standardized entity to ensure cohesiveness of records across patients.

A phrase match for "lumpectomy" may be recognized as a shorthand term synonymous with the more specific "Lumpectomy of breast (procedure)". A desired specificity may be required for the assigned entity which contains the most prominently used term for a procedure. Similarly to interstitial brachytherapy, manual or automated curation may assign all shorthand forms of an entity with a standardized entity.

In one example, a patient record may include the sentence, "Patient has a history of hypertension and type 2 diabetes."

| Text | Concept Type | Matched Concept | Canonical Concept | UMLS CUI | Concept Name |
|---|---|---|---|---|---|
| hypertension | Comorbidities | SNOMEDCT_US#38341003 | SNOMEDCT_US#38341003 | C0020538 | Hypertension |
| type 2 diabetes | Comorbidities | CHV#0000003837 | SNOMEDCT_US#44054006 | C0011860 | Diabetes Mellitus, Non-Insulin Dependent |

Not all phrases will map to a non-authoritative source or a phrase which lacks a desired specificity. In this instance, "hypertension" is a direct match within a source of authority and may be assigned without normalization to another ontology.

A colloquial phrase match for "type 2 diabetes" may be references for an AUI in the CHV vocabulary. A relational relationship may exist in the ontology for linking the CHV ontology match with a source of authority. Such predefined relationships may be referenced and traversed. In some instances, the relationships must be manually approved or white-listed to allow traversal. An approval or white-listing is an indication that the relationship maintains accuracy with the original mapping and does not result in information loss such as a change in the scope of meaning between any linked phrases. One such relationship may include a "is informal" relationship. In this case, "Diabetes Mellitus, Non-Insulin Dependent" may be the entity having a technical term linked as a formal phrasing.

In one example, a patient record may include a sentence, "After the patient's lumpectomy to remove an area of Ductal Carcinoma in Situ, they will receive brachytherapy."

In some embodiments, direct mapping may not be possible based on a phrase alone. Inferences may be derived, either through manual curation or machine learning, to utilize contextual presence of lumpectomy procedure and Ductal Carcinoma in Situ tumor characterization to support an inference that the primary cancer site is breast.

relating to a preferred vocabulary may be assigned. Additionally, metadata with the assigned entity may reference cancer site breast.

In one example, "Ductal Carcinoma in Situ" may be defined in multiple vocabularies. Phrase matching may return a hit to all matched vocabularies, or may return a hit to the first matched vocabulary. Each vocabulary may be mapped to SNOMED due to its completeness and a SNOMED entity assigned. Similarly, metadate with the assigned entity may reference cancer site breast.

As disclosed above, "brachytherapy" may be a direct match that does not require additional normalization steps as the phrase match is already from an authoritative source and is specific to radiotherapy.

Inferences may be generated when metadata of associated concepts, such as those concepts in the same paragraph or sentence, repeatedly indicate a certain feature (cancer site of the breast), an inference may be drawn that a feature without a phrase match is identified and converted to a structured format. Here, because multiple phrase matches indicated breast cancer must be present to receive the procedure or directly reference a tumor which by its very nature must be of the breast, an inferred primary cancer site may be assigned for breast.

Returning to FIG. 1, the post-processing pipeline stage 170 may receive a listing of all the structured entities and generate a response/report. For example, a response may be formatted into an output divided into several sections, each section relating to, for example, the fields of Diagnosis, Procedures, Radiology, etc., as discussed above. Under a Diagnosis header/identifier, structured entities relating to diagnosis may be summarized with the final normalized entity, information from the entity structuring, and any confidence values generated during the classification and/or ranking/filtering. The response may include all of the sections with corresponding structured entities. The response may be generated and output, e.g., as a word document, a

| Text | Concept Type | Matched Concept | Canonical Concept | UMLS CUI | Concept Name |
|---|---|---|---|---|---|
| lumpectomy | Surgical Procedure | NCI#C15755 | SNOMEDCT_US#64368001 | C0851238 | Lumpectomy of breast (procedure) |
| Ductal Carcinoma in Situ | Tumor Characterization | NCI#C2924 | SNOMEDCT_US#128879006 | C1266022 | Ductal Carcinoma in Situ |
| brachytherapy | Radiotherapy Modality | SNOMEDCT_US#399315003 | SNOMEDCT_US#399315003 | C0851238 | Brachytherapy |
| <inferred> | Primary Cancer Site | | SNOMEDCT_US#94012007 | C0346742 | Breast |

In one example, a phrase "lumpectomy" may be recognized as a shorthand term, synonymous with the more specific "Lumpectomy of breast (procedure)". An entity spreadsheet, or a JavaScript Object Notation (JSON) file with each of the relevant sections and structured entities encoded therein.

The MLA and DLNN algorithms described herein may be implemented using supervised, unsupervised, and/or semi-supervised approaches. Patient/document classification based off of text classification is the general task of processing text and identifying whether it belongs to one of many pre-defined groups (e.g., the above-referenced medical fields). For example, supervised machine learning methods may be used to classify patients as Male or Female, because many clinical documents exist for patients whose genders are known. Exemplary non-machine learning ways of determining a gender would be to apply a regular expression for "Gender:" in text or "pt is a ##yo X". It would be an exhausting endeavor to create a regular expression for every potential combination of words or characters that gender may be mentioned in text in order to be able to extract it using simple text matching. Instead, a simple heuristic component for classifying a gender may be to determine the ratio of male vs female pronouns in text, under the assumption that references in medical text are almost entirely describing the patient (as opposed to their family members or medical staff, who are occasionally mentioned as well).

Similarly, a supervised machine learning method may require that the gender is known or provided for some batch of patients. The machine learning method may then extract signals or features from the text that are indicative of the gender. At that point, a Naive Bayes MLA may be utilized to, for example, identify the ratio of male vs female pronouns. The Naive Bayes MLA may determine the frequency of every word that occurs in any clinical document occurs in the male documents vs how often the same words occur in the female documents in terms of probability (e.g., 'he' is 2% of words in male documents and 0.1% of female documents). Once trained, for each new document to be classified, the Naive Bayes may use the generated probabilities/statistics to determine the likelihood that a document falls within the male linguistic probability distribution or the female distribution. A general threshold value or comparison may be applied to determine whichever probability is higher.

While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. Returning to the example regarding gender, an unsupervised approach may attempt to identify a natural divide of documents into two groups without explicitly taking gender into account. On the other hand, a drawback to a purely unsupervised approach is that there's no guarantee that the division identified is related to gender. For example, the division may be between patients who went to Hospital System A and those who did not.

As a result, semi-supervised methods may be the most optimal approach whenever there are a large number of unlabeled or unannotated documents as well as labeled documents in the training set. EMRs/EHRs may be particularly well-suited to this approach, because hospitals take care to note key health information for each patient. For example, considering a practical approach to applying a semi-supervised MLA, presume that an exemplary dataset generates a probability distribution such that "he" accounts for 2% of the words in male patients' documents and 0.75% of female patients' documents. If these estimates were taken over a small number of patients (e.g., 100 pages of text total), but 80 of these pages are from female patients, the probability distribution may be quite susceptible to noise (i.e, erroneous weighing) and may generate wrong or undesirable results.

The unsupervised approach solves this by providing a number of documents from patients whose genders unknown, effectively allowing the MLA to learn something about language in general. Specifically, the MLA determines how frequent "he" may be presented in clinical text in general. If the semi-supervised MLA identifies that "he" only occurs 0.5% of the time, "he" may be occurring unusually frequently in the labeled documents (e.g., at 2% and 0.75% probability distribution). For example, no ratio of male-to-female patients could balance out to 0.5% given an initial probabilities of 0.75% and 2%. Instead, the MLA corrects for the noise in the data set by applying the information that there were more female patients than male patients and accordingly adjust the probabilities more strongly for the male probability distributions than the female. A scaled probability distribution may indicate that "he" occurs at 0.9% frequency in male patient files and 0.1% in female patient files, so that the average distribution of "he" is 0.5%. The semi-supervised MLA may then accurately apply the heuristic technique as a portion of the classification determination.

Machine learning algorithms and deep learning neural networks tend to provide approximate solutions to any complex problem without a clear set of rules to constrain the problem through. MLA and DLNN are most useful for problems which are too difficult to constrain accurately to a few simple rules/constraints and excel at finding unique solutions to these complex problems. These unique solutions may also include equally unique bugs for edge cases of the unique solution, which may require fine tuning to improve the performance of the MLA by adding better/more accurate/more representative training data, by tuning hyperparameters, or by improving or replacing the MLAs themselves.

In an exemplary model, as described below with reference to FIG. 8, a training feedback loop operates to improve the training data set by improving the annotations of the edge cases and using the improved training data to refine the MLA model itself. For example, an initial MLA trained on an initial data set may be only 75% accurate at its given task. By directly utilizing the MLA in a platform where humans are entering data based on clinical documents for patients, edge cases (erroneous output) may be identified, the annotations surrounding the documents/patients of the edge case may be improved, and the improvements submitted back into the MLA to further train the model to improve accuracy. Regardless of whether the human agrees or disagrees with the machine learning model's prediction/classification, the human takes into account the prediction as well as other information in the clinical documents before making their final annotation. This final annotation is utilized as the "gold standard" by which the MLA should operate and can immediately add the labeled documents and the corresponding annotation to the training data set to improve the results when the MLA is trained in the future. Each edge case that is corrected by a human, even each additional question that a human answers above and beyond the erroneous outputs may directly help the machine learning model answer the corresponding question correctly in the future.

The feedback process may be improved by adding the ability to collect direct feedback from an annotator. For example, if the annotator agrees with the machine learning model's prediction, then it may be presumed that the prediction was correct. Conversely, if the annotator disagrees with the prediction, it may not be clear why the MLA prediction was wrong. For example, the MLA may make an erroneous prediction if the documents were for the wrong person, if OCR errors exist which confounded the prediction, or if the model simply was not sufficiently trained to make a correct prediction from the data in that instance.

Figure 8:
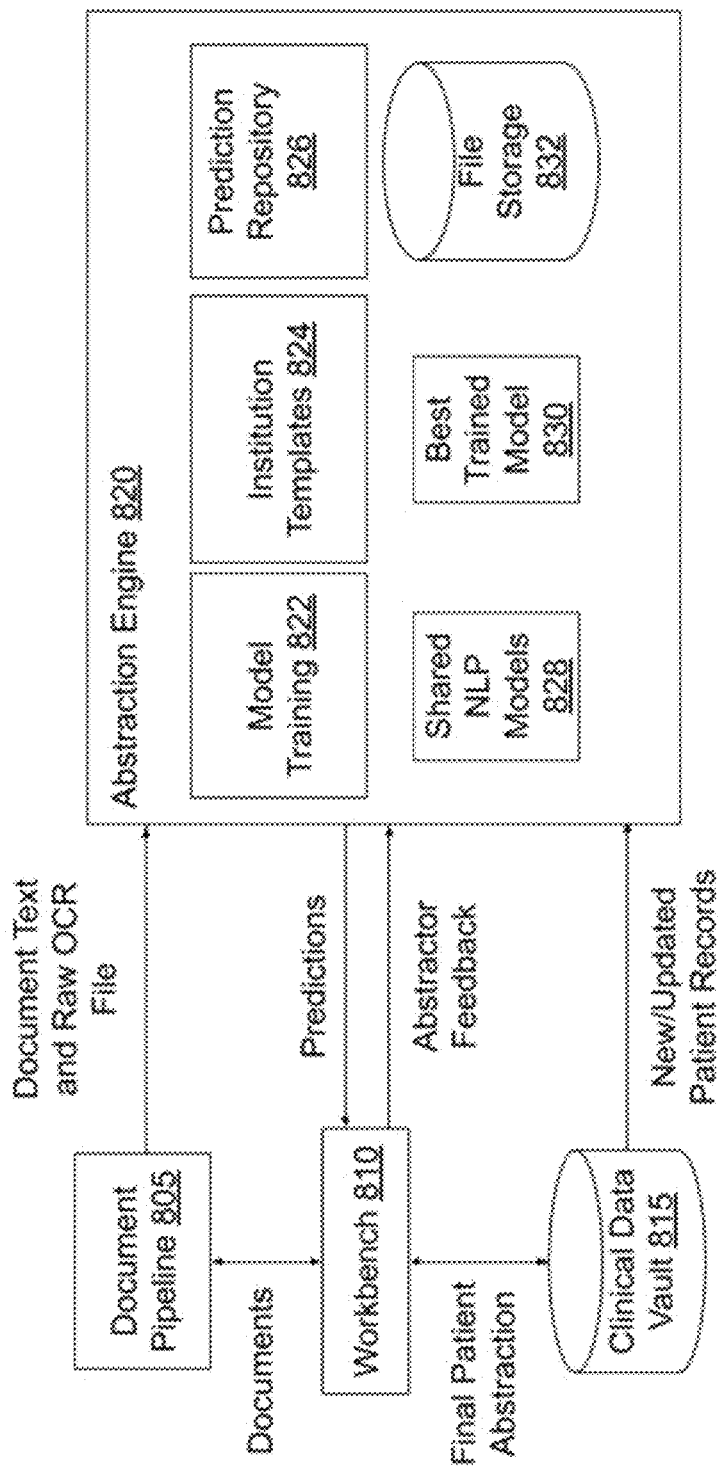
FIG. 8 is an exemplary architecture for implementing an embodiment of the pipeline of FIG. 1.

Turning now to FIG. 8, an exemplary system architecture is depicted. In particular, FIG. 8 depicts a scenario in which the system receives documents, for example, from a Clinical Data Vault 815, new documents from a Document Pipeline 805, or corrected documents via the Workbench 810 (introduced below), uploads documents, and posts them to a server that coordinates a number of tasks and manages the intake of documents for the intake pipeline described in FIG. 1.

From there, and within the Document Pipeline 805, the documents are posted to another server that stores sensitive files and authenticates all access to those files. Concurrently, a copy of each of the documents is sent to a converter, which patches each document with a viewable image, e.g., a PDF, of the document. The system calls an OCR service, such as Google Cloud Vision or Tesseract, which runs optical character recognition on the documents. Alternatively, if the system determines that the document was already OCRed, a cached copy of the OCR document is retrieved from a database, such as the File Storage 832. The viewable image file then is linked with the original file. Similarly, a copy of a searchable text version of the document is provided from the OCR service to combine with the original document and the viewable image from the converter and, if not previously OCRed, a second copy of the searchable text version is transmitted to the database where it is cached. The Abstraction Engine 820 and its toolbox components utilize MLA and NLP to generate predictions.

Once the patient documents are processed in the Document Pipeline 805, Workbench 810, and then processed through OCR, raw OCR information may be pulled from the database. The processing intake pipeline stage for pre-processing and OCR occurs in these servers/processes. The system also may check the database to determine whether improved NLP models have been provided and retrieve any new or updated models. The system then applies the most current NLP algorithms and models to the raw OCR files. In this regard, patient data may be encoded differently depending on the project for which it is being used, so the system may communicate with a service (e.g., the Institution Templates 824 module) that includes one or more templates to set forth how the OCR'd data should be abstracted and which values within that data are displayed for each field. Tabular and template extraction may also be contained within a database within the Institution Templates 824 module.

The predictive data is then tailored for the given project from the tabular extraction applied, and those predictions then are posted to a second database (e.g., a database within the Abstraction Engine 820 for use by one or more additional applications. The system may specify a global encoding list for all of the concepts related to each of the dictionaries/ databases and the internal universal dictionary (e.g., medical concepts and fields described above). Using medications as an example, the system specifies all of the medication ingredients that may be beneficial for analysis.

By narrowing the search to a targeted list of concepts that are important to identify, overall processing speed of the architecture may be improved. For example, UMLS metadata may be applied to determine that "Tylenol" is a brand name drug, "acetaminophen" is a generic ingredient as described above. When "Tylenol" is recognized as a medication, medication-specific queries may be processed to identify normalization candidates, for example, within the Abstraction Engine 820. If a query returns that "acetaminophen" is within the system but "eucalyptus leaves" is not, any medication determined to be eucalyptus-based may be ignored by the system.

The Workbench 810 may represent a server for maintaining a user interface (UI) to implement a patient record analysis system responsible for managing the flow of information between systems of the instant architecture and/or stage of the processing pipeline. An exemplary high-level description of the UI may include three windows/panes, e.g.: a center pane that allows an abstractor to view patient documents for which the other two panes may display information relating to. A left pane may be configured for entering the abstracted information, including fields (i.e., drop-down lists), dates can be entered and subjected to rules for validation (e.g., DOB must be before date of death), singular fields (e.g. patient's gender or primary cancer diagnosis), repeatable fields (e.g. drugs the patient took, surgeries, etc), fields with sub-fields (e.g. medication structured data, cancer diagnoses, etc. as disclosed above with reference to FIG. 2). A right pane may be configured for displaying Abstraction Engine 820 results. The way these are structured is determined by the Abstraction Engine 820 configuration. Category groups fields at a high level and specifies, for example, four of them currently: Demographics, diagnosis, treatments, outcomes. Categories have many fields, which are what the abstractors are trying to enter values for. These fields may also be expanded and collapsed. When expanded, a list of values that the Abstraction Engine 820 predicted for that field (and optionally, a confidence score specified for that value) may be shown. Fields can also have justifications tied to them, which are text snippets that the Abstraction Engine 820 determines best shows why the given value is correct for the given field. Given that many of the predictions are tied to the intake pipeline stages, the text surrounding the identified concept candidate may be provided as the justification.

Workbench 810, the patient record analysis system, may access and/or retrieve patient data from a patient record located in a workflow component, such as the Clinical Data Vault 815, or from the patient record including the documents that were stored in the Document Pipeline 805. For each document, the Workbench 810 may also retrieve the corresponding NLP predictions from the Abstraction Engine 820, e.g., from the Prediction Repository 826. Once abstracted, the final abstraction report and data may be transmitted to the Clinical Data Vault 815. For example, the MLAs may have already provided classifications/predictions for the patient that is being abstracted. The Abstraction Engine 820 may have already processed all of the documents for the given patient, generated its predictions, and uploaded them to the Prediction Repository 826. The Workbench 810 server may then retrieve the patient documents as well as Abstraction Engine 820 predictions for each patient. An abstractor may use an interface of the Workbench 810 for manual abstraction. The Abstraction Engine 820 pipeline may be further optimized such that the Workbench 810 interface also includes machine learning predictions for each template's fields and presents them to the abstractors (e.g., the fields of FIG. 2). Once identifications of relevant metadata for clinical concepts are found in text, the Abstraction Engine 820 may generate predictions. Once entity normalization has been completed, a report may be generated and stored in the Clinical Data Vault 815, for example, in a text file or a JSON format. This information may be populated for every medication that is identified in the patient's clinical documents and may also be provided to the Abstraction Engine 820 for storing this information in a protected database. Other services can then query the Abstraction Engine 820 by Patient or by Document and determine which clinical predictions the Abstraction Engine 820 has made. The Abstraction Engine 820 implements the parser, entity linking, and entity normalization intake pipelines stages.

As mentioned above, the system periodically checks to make sure that the NLP/MLA models being used are most up-to-date (e.g., elements 135, 145, and 155 from FIG. 1). The system may include a bootcamp subroutine, e.g., within the Shared NLP Models 828 module, for evaluating and updating the NLP and MLA models. In this subroutine, the system retrieves clinical record documents from the clinical data vault, e.g., based on one or more unique user id's, on clinical features common to one or more patients, or any other criteria. The subroutine also may communicate with the File Storage 832 database to retrieve the raw OCR files corresponding to each of those documents, as well as the current NLP model. The system further may retrieve abstractor feedback (e.g., the feedback loop's erroneous result corrections/annotations) from the toolbox. Each of these inputs may be used to execute a training script to verify or update the NLP model. At that point, metadata relating to the updated model may be communicated to the Model Training 822 module (e.g., for later human inspection, model or data provenance, and/or long-term metrics). The Workbench 810 supports the ability for abstractors to tag the Abstraction Engine's 820 incorrect predictions with a predetermined set of issues (e.g., documents are from wrong patient, OCR errors, wrong entity linked, correct concept candidate, wrong entity linked, correct concept candidate but hypothetical reference in document cannot be construed as haven taken place, etc.). For example, in the case of patients whose predictions are incorrect because 'Documents are for wrong patient', the Model Training 822 module may ignore these patients when training future MLAs to understand gender or may instantiate a specific training phase to train the current MLAs to predict which patients have documents from multiple patients and exclude from training and/or flag all patients which have documents from wrong patient for independent abstraction.

Similarly, other tags such as 'Bad prediction due to OCR error' may be applied as feedback on a given OCR software/service, which means the system can implement various OCR services and use abstractor feedback to determine the highest quality OCR service from various competitors. The Abstraction Engine 820, Workbench 810, and Document Pipeline 805 together implement the Entity structuring and post processing intake pipeline stages.

The Workbench 810 facilitates and incorporates human abstraction by providing prediction justifications and confidence metrics alongside the predictions. A number of issues arise when providing an abstractor with only a single list of possible answers and corresponding confidence values. For example, an abstractor may not be provided with any reasoning about how the predictions or confidence values are calculated, or it may not be clear when an abstractor should trust the NLP models and when they should take a deeper look into the patient record because it is difficult to know what confidence level is needed before an output needs to be verified for accuracy. Instead of making this decision the sole responsibility of the abstractor, Abstraction Engine is designed to provide justifications for its predictions in the form of textual contexts that are determined to indicate that a prediction is correct.

Following the example of structuring a full medication entry that included a Text Context field (i.e., FIG. 1), additional processing may determine whether the fully structured concept is a positive mention (e.g., it is not related to a family member's previous illness or treatments, it is not a hypothetical treatment proposed by a doctor, it is not a diagnosis unrelated to the patient that happens to be mentioned in supplemental literature, etc.) and maintaining links to text context may be a useful justification to the positive mention. This determination may be processed through other text classification algorithms that use the contextual information to identify whether the concept mention is positive or negative. For example, the simplest implementation may include a pattern-based system configured to ignore diagnoses in contexts such as "{mother/father/sister/etc} has a history of {disease}." While these phrases may be considered in the NLP algorithm itself, error checking may involve repeating the process in low confidence predictions, or providing additional algorithms with text classifiers that utilize the additional textual context. Another embodiment may involve aggregating all of the mentions of a primary cancer site which may also include all or some of the textual contexts for those mentions, which can provide the abstractor with confidence that the prediction was correct without manual intervention.

Referring again to FIG. 8, patient upload, prediction generation, abstraction, and feedback and training processes of the instant architecture are disclosed. In particular, this figure illustrates a process in which Patient documents stored in Clinical Data Vault 815 may be sent to Workbench 810 and then to the Document Pipeline 805. OCR may run either an OCR service such as Google Cloud Vision or Tesseract to OCR documents or, if the document was previously OCRed, it may retrieve a cached copy of the OCR from within the Abstract Engine 820. OCR may patch the documents with a searchable text version of the PDFs, and OCR may cache the raw OCR files to the Abstraction Engine File Storage 832.

Once the patient documents are processed, the Abstraction Engine 820 may pull raw OCR files from its File Storage 832, check the File Storage 832 for improved NLP models and pull them if necessary, run the documents through its current NLP pipeline and models (including Best Trained Model 830), pull project-specific templates from Institution Templates module 824, tailor its final predictions for the given project, and post those predictions and related metadata to its Prediction Repository 826. In this regard, patients may be encoded differently in each project, so the Institution Templates module 824 may be a service that coordinates project encodings (e.g. which fields are abstracted, which values are displayed for each field).

When a Workbench user loads a patient, Workbench 810 may pull the patient record from the Document Pipeline 805. Workbench 810 also may pull the corresponding Abstraction Engine predictions from the Abstraction Engine Prediction Repository 826 (if the predictions are available). The Workbench 810 may abstract data field by field and pass patient data to the Document Pipeline 805. Patients may provide direct feedback about specific NLP predictions, which will be passed directly to the Abstraction Engine 820 to assist future training using the Model Training module 822. Final abstraction reports and data then may be stored in the Clinical Data Vault 815.

In order to accomplish feedback and training processes, the Model Training module 822 within the Abstraction Engine 820 may periodically update Abstraction Engine NLP models, including the Shared NLP Models 828 and the Best Trained Model 830. Specifically, the Model Training module 822 may be initialized by a script or a periodic update protocol. The Model Training module 822 also may pull: clinical records from the Clinical Data Vault 815 for a list of patient UUIDs specified by script/protocol, the raw OCR files that correspond to each of these patients' documents from the Abstraction Engine File Storage 832, and existing NLP models from File Storage 832 (some models can be trained multiple times and improve over many iterations of new data). Abstractor feedback may be pulled from Workbench 810 into the Abstraction Engine 820 for additional training info. The Abstraction Engine 820 may execute its training script and post NLP models to File Storage 832 and also post model metadata for human inspection, model/data provenance, and long-term metrics.

Figure 9:
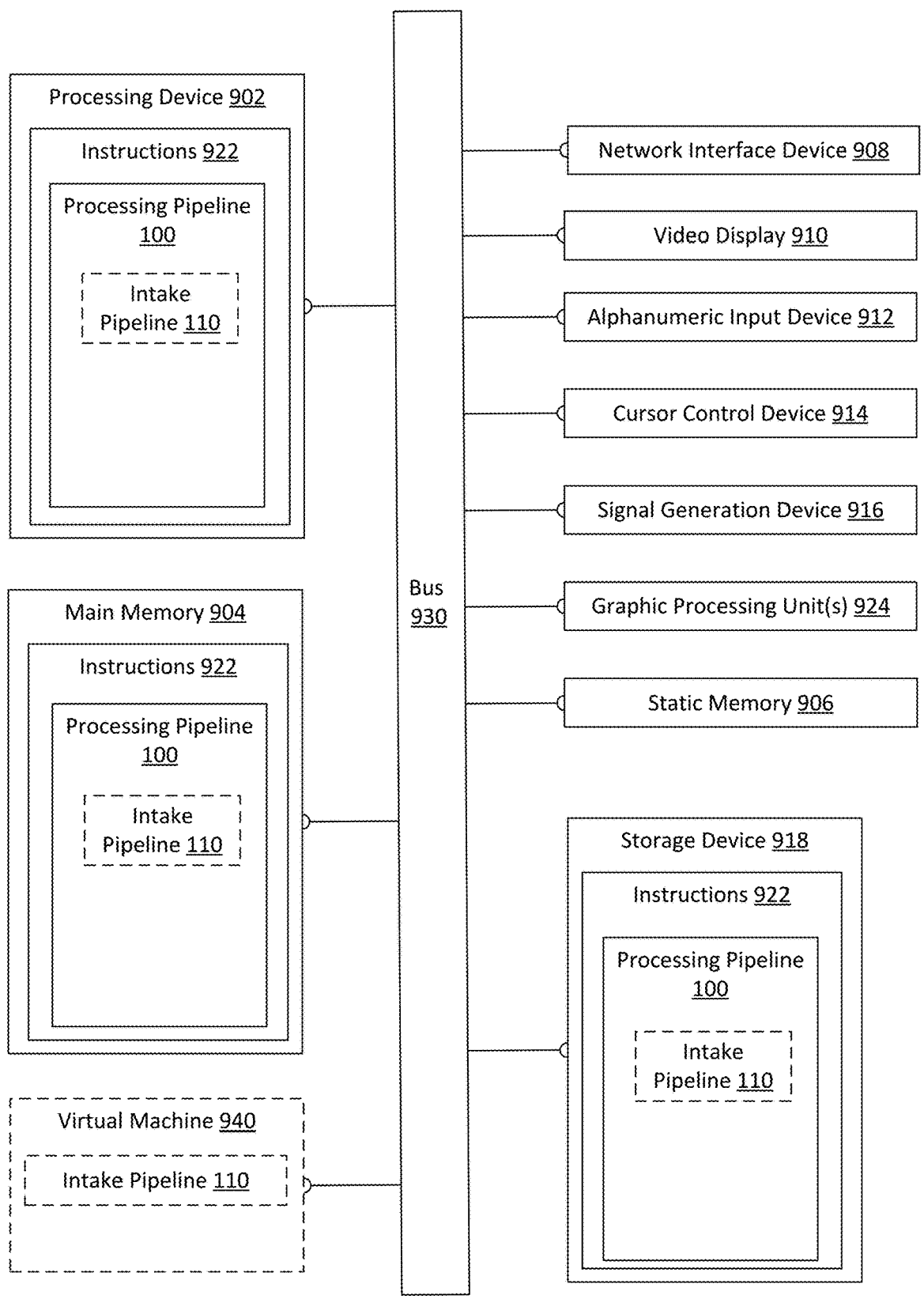
FIG. 9 is an exemplary system diagram for implementing the methods disclosed herein.

Turning now to FIG. 9, an illustration of an example machine of a computer system 900 within which a set of instructions, for causing the machine to perform any one or more of the methodologies discussed herein, may be executed. In alternative implementations, the machine may be connected (such as networked) to other machines in a LAN, an intranet, an extranet, and/or the Internet.

The machine may operate in the capacity of a server or a client machine in client-server network environment, as a peer machine in a peer-to-peer (or distributed) network environment, or as a server or a client machine in a cloud computing infrastructure or environment. The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 900 includes a processing device 902, a main memory 904 (such as read-only memory (ROM), flash memory, dynamic random access memory (DRAM) such as synchronous DRAM (SDRAM) or DRAM, etc.), a static memory 906 (such as flash memory, static random access memory (SRAM), etc.), and a data storage device 918, which communicate with each other via a bus 930.

Processing device 902 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. The processing device 902 is configured to execute instructions 922 for performing the operations and steps discussed herein.

The computer system 900 may further include a network interface device 908 for connecting to the LAN, intranet, internet, and/or the extranet. The computer system 900 also may include a video display unit 910 (such as a liquid crystal display (LCD) or a cathode ray tube (CRT)), an alphanumeric input device 912 (such as a keyboard), a cursor control device 914 (such as a mouse), a signal generation device 916 (such as a speaker), and a graphic processing unit 924 (such as a graphics card).

The data storage device 918 may be a machine-readable storage medium 928 (also known as a computer-readable medium) on which is stored one or more sets of instructions or software 922 embodying any one or more of the methodologies or functions described herein. The instructions 922 may also reside, completely or at least partially, within the main memory 904 and/or within the processing device 902 during execution thereof by the computer system 900, the main memory 904 and the processing device 902 also constituting machine-readable storage media.

In one implementation, the instructions 922 include instructions for a Processing Pipeline (such as the Processing Pipeline 100 of FIG. 1) and/or a software library containing methods that function as a Processing Pipeline. The instructions 922 may further include instructions for an Intake Pipeline Module (such as the Intake Pipeline Module 110 of FIG. 1) While the machine-readable storage medium 928 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine readable storage medium as a transitory storage medium or transitory machine-readable storage medium.

In another implementation, a virtual machine 940 may include a module for executing instructions for an Intake Pipeline Module (such as the Intake Pipeline Module 110 of FIG. 1). In computing, a virtual machine (VM) is an emulation of a computer system. Virtual machines are based on computer architectures and provide functionality of a physical computer. Their implementations may involve specialized hardware, software, or a combination of hardware and software.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices. The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

The systems described above may have multiple uses that are beneficial to clinicians and researchers involved in the treatment of diseases, research into diseases, and data analysis involving disease. One example is in the field of clinical trials. A clinical trial is a research study to determine the safety and efficacy of a drug, device, biologic, or other potential treatment. Clinical trials often have inclusion and exclusion criteria, whereby a patient must meet all of the inclusion criteria and not have any of the exclusion criteria in order to enroll in the study. Many clinical trials have specific criteria that can be determined only after close examination of the medical record. For instance, an example of inclusion criteria for a study of chemotherapy of breast cancer subjects might be postmenopausal women between the ages of 45 and 75 who have been diagnosed with Stage II breast cancer. An exclusion criterion for this study may include a positive identification for abnormal renal function, if, for example, one or more of the drugs used as treatment in the study are nephrotoxic. A medical institution, such as a hospital, may have many patients who are eligible for the study, but require the system described above in order to parse their EHR in order to prepare a list of patients who are eligible to participate in the study. The clinical trial systems and methods described herein may be operated upon and/or utilized in connection with the systems and methods described in U.S. Provisional Patent Application No. 62/855,913, titled Systems and Methods of Clinical Trial Evaluation, filed May 31, 2019, the contents of which are incorporated herein by reference and in their entirety.

Another example relates to the development of synthetic control arms for clinical trials. In a clinical trial, a group of patients (called the "control group") receives standard of care treatment while a second group (the "experimental group") receives an experimental treatment (such as a study drug). Often, a study is "blinded" meaning the patients who enroll in the study do not know if they are part of the control group or the experimental group. It can be difficult to recruit patients to clinical trials because many patients wish to ensure they are part of the experimental group. An institution may utilize the systems and methods described herein in order to create a list of structured data from each patient in the EHR who meets the inclusion/exclusion criteria. By leveraging the existing data of patients who do not qualify for the clinical trials, a propensity based model may supplement the clinical trial data as the control arm of the study. These patients may be considered the control group, and their health data as captured in structured format may be utilized as the control arm of the study. In this way, a separate enrolled control group is not needed for the study, and the patients who enroll may all be made part of the experimental group.

Another example relates to data analysis of an institution's EHR. Many institutions, such as hospitals, retain patient health information in free text that is not easily searchable for patterns in treatment or outcomes. Using the systems above, institutions may be able to create structured data sets with data elements that permit the institution to conduct sophisticated data analysis to look for data trends. Such trends may indicate best practices in particular departments, or may indicate areas of concern that require the institution to conduct further investigation. For example, the institution may utilize the systems and methods described above in order to determine which patients are being prescribed which medications at which dosages. The systems and methods may be used periodically (for instance, on a quarterly basis), to analyze utilization rates. As another example, the institution may utilize the systems and methods described above in order to characterize the outcomes of patients with respect to treatments which they have been prescribed and undertook while under the care of the institution. The analysis may be conducted in a way that the structured data generated by the systems and methods described above omits certain data elements in order to ensure that the structured data is de-identified or that protected health information is securely maintained, encoded, or removed. For instance, name, address (all geographic subdivisions smaller than state, including street address, city, county, and zip code), elements (except years) of dates related to an individual (including birthdate, admission date, discharge date, date of death, and exact age if over 89), telephone numbers, fax number, email address, Social Security Number, medical record number, health plan beneficiary number, account number, certificate or license number, any vehicle or other device serial number, web URL, Internet Protocol (IP) address, finger or voice print, or photographic image of the patient, may all be omitted from structured data fields. Alternatively, or in addition, the resulting data may be run through a statistical system to ensure there is a very low chance it contains identifiable health information. Once de-identified, the institution may provide the data to a third party for further analysis or other use.

In another example, an institution may utilize the systems and methods described above to conduct automatic quality checks on the information contained in its medical record. For instance, the institution may use the systems and methods to compare information in one section of the medical record with information in another section of the medical record to ensure consistency between the records in each section. As an example, imaging reports on cancer tumors can contain radiology information about the tumor (such as its size), while a radiology report prepared by a physician may also contain similar information. The systems and methods described herein may be used to ensure that the imaging report (for instance, the tumor diameter is 2 cm) is consistent with the information as the radiology report (for instance, the tumor diameter is 2 cm). If the information is different, an alert may be triggered to have a clinician review the record further.

In another example, other types of records could be used instead of patient records to create a structured set of data from unstructured information. One type of record that could be analyzed using the systems and methods described above is a scientific journal publication. Many publications disclose information about new and potentially promising treatments in cancer and other diseases. Other publications disclose information about existing treatments that may be useful for newly indicated diseases. The systems and methods described herein may be used to automatically generate a list of structured data from a scientific publication (for instance, it may generate a list of structured data indicating that a certain drug is effective at a certain dosage for a certain class of patients). The list of structured data may be combined in a knowledge database comprising other similar lists of data.

In another example, the systems and methods described herein may produce structured data that can be aggregated, and the results of the aggregation may be analyzed for comparative purposes. One exemplary use is for population health purposes. For instance, the systems and methods described herein may be used to compare aggregated structured data from one institution with aggregated structured data from another institution or another group of institutions. Such comparison may be useful when determining medication utilization rates; duration of inpatient stays; rates of readmission; types and frequencies of diseases, such as cancers; or other indicators. As another example, the systems and methods described herein may be used to compare aggregated structured data from one geographic area with aggregated structured data from another geographic area. Structured data from an institution or a geographic area may be aggregated using methods known in the art.

The systems and methods described herein may be operated upon and/or utilized in connection with the systems and methods described in U.S. Provisional Patent Application No. 62/746,997, titled Data Based Cancer Research and Treatment Systems and Methods, filed Oct. 17, 2018, U.S. Non-Provisional patent application Ser. No. 16/657,804, titled Data Based Cancer Research and Treatment Systems and Methods, filed Oct. 18, 2019, U.S. Pat. No. 10,395,772, titled Mobile Supplementation, Extraction, and Analysis of Health Records, issued Aug. 27, 2019, and U.S. Non-Provisional patent application Ser. No. 16/531,005, titled Mobile Supplementation, Extraction, and Analysis of Health Records, filed Aug. 2, 2019, the contents of which are incorporated herein by reference and in their entirety.

While the invention may be susceptible to various modifications and alternative forms, specific embodiments have been shown by way of example in the drawings and have been described in detail herein. However, it should be understood that the invention is not intended to be limited to the particular forms disclosed. Thus, the invention is to cover all modifications, equivalents, and alternatives falling within the spirit and scope of the invention as defined by the following appended claims.

To apprise the public of the scope of this invention, the following claims are made:

1. A method for generating structured records of a patient's health record, comprising:

receiving, at a processor, the patient's health record from an electronic health record system;

selecting, by the processor, an artificial intelligence model trained on electronic health records from one or more artificial intelligence models based on a type of document being evaluated by the processor;

determining, by the processor via an abstraction engine applying the selected artificial intelligence model, a first concept from a text of the health record, the first concept relating to the patient;

identifying a match to the first concept in a first list of concepts, wherein the first list of concepts is not designated as a predetermined authority and includes two or more tiers of concepts;

referencing the first concept with an entity in a database of related concepts;

identifying a match from the entity to a second concept in a second list of concepts designated as the predetermined authority and including two or more tiers of concepts, wherein the second concept is included in one of the two or more tiers of the predetermined authority, and wherein the predetermined authority is not directly linked to the first list of concepts except by a relationship to the entity;

retrieving, by the processor, a degree of specificity comprising selection criteria identifying one or more tiers of the two or more tiers of the predetermined authority, other than the tier including the second concept;

normalizing the second concept to a third concept included in the one or more other tiers, based at least in part on the second concept not satisfying the selection criteria;

providing the third concept as an identifier of the patient's health record, wherein the first, second, and third concepts and the identifier each have a respective category; and generating, by the processor, a structured record from the identifier.

2. The method of claim 1, wherein the respective category categories of the first concept, the second concept, the third concept, and the identifier are categorized as one of diagnosis, primary diagnosis site, metastatic diagnosis site, tumor characterization, standard grade, alternative grade, medications, surgical procedure, smoking status, comorbidities, adverse events, outcomes, performance scores, radiotherapy modality, radiotherapy units, imaging type, gene mention, immunology markers, TNM status, or AJCC stage.

3. The method of claim 1, wherein the first list of concepts is one of a vocabulary, terminology, ontology, or code set.

4. The method of claim 3, wherein the predetermined authority is another one of a vocabulary, terminology, ontology, or code set.

5. The method of claim 4, wherein the first list of concepts is an ontology, the predetermined authority is an ontology, and the ontology of the first list of concepts does not directly link to the ontology of the predetermined authority.

6. The method of claim 5, wherein the ontology of the first list of concepts not directly linking to the ontology of the predetermined authority signifies a lack of one of a hierarchical relationship or a non-hierarchical relationship and wherein a non-hierarchical relationship is a link comprising one of physically related to, spatially related to, temporally related to, functionally related to, or conceptually related to.

7. The method of claim 1, wherein the entity in the database of related concepts is a concept in one of a vocabulary, terminology, ontology, or code set.

8. The method of claim 7, wherein the entity has a first non-hierarchical relationship link between the entity and the first concept and a second non-hierarchical relationship link between the entity and the second concept.

9. The method of claim 8, wherein the first non-hierarchical relationship link is a link comprising one of physically related to, spatially related to, temporally related to, functionally related to, or conceptually related to and the second non-hierarchical relationship link is a link comprising one of physically related to, spatially related to, temporally related to, functionally related to, or conceptually related to.

10. The method of claim 1, wherein an identifier is a field having a structured format, the field encoding the second concept in the structured format.

11. The method of claim 1, wherein the predetermined authority is one of a reference vocabulary, reference terminology, reference ontology, or reference code set.

12. The method of claim 11, wherein the predetermined authority is categorized as one of diagnosis, primary diagnosis site, metastatic diagnosis site, tumor characterization, standard grade, alternative grade, medications, surgical procedure, smoking status, comorbidities, adverse events, outcomes, performance scores, radiotherapy modality, radiotherapy units, imaging type, gene mention, immunology markers, TNM status, or AJCC stage.

13. The method of claim 1, wherein the first list of concepts is a medicine ontology, the entity is a medicine, and the predetermined authority is a reference medicine ontology.

14. The method of claim 1, wherein the first list of concepts is a procedure ontology, the entity is a procedure, and the predetermined authority is a reference procedure ontology.

15. The method of claim 1, wherein the first list of concepts is an outcomes ontology, the entity is an outcome, and the predetermined authority is a reference outcome ontology.

16. The method of claim 1, wherein the first list of concepts is a medicine ontology, the entity is a treatment, and the predetermined authority is a reference diagnosis ontology.

17. The method of claim 1, wherein the first list of concepts is a unified medical ontology, the entity is a medicine, and the predetermined authority is a reference medicine ontology.

18. The method of claim 1, wherein the first list of concepts is a brand-name medicine ontology, the entity is a medicine, and the predetermined authority is a generic medicine ontology.

19. The method of claim 1, wherein generating the structured record from the identifier comprises:
   identifying a structured format for the identifier of the patient's health record;
   extracting fields from the structured format;
   assigning one or more values associated with the second concept to the extracted fields;
   identifying one or more values from the text of the health record surrounding the first concept;
   assigning one or more of the identified values to the extracted fields; and
   providing the structured format having one or more assigned values as a structured record of the patient's health record.

20. The method of claim 1, wherein the third concept is categorized as one of diagnosis, primary diagnosis site, metastatic diagnosis site, tumor characterization, standard grade, alternative grade, medications, surgical procedure, smoking status, comorbidities, adverse events, outcomes, performance scores, radiotherapy modality, radiotherapy units, imaging type, gene mention, immunology markers, TNM status, or AJCC stage.

21. The method of claim 1, wherein the predetermined degree of specificity is based at least in part on metadata of the second concept.

22. The method of claim 19, wherein the one or more values are extracted from sentences of the text using natural language processing (NLP).

23. The method of claim 1, wherein the referencing the first concept and the normalizing of the second concept are precomputed for all concepts and cached for fast retrieval.

24. A method, comprising:
   performing the method of claim 1 in an electronic health record system.

25. The method of claim 24, wherein the predetermined authority is a cancer ontology.

26. The method of claim 25, wherein the structured record is based at least in part on a result from a next-generation sequencing of a subject tumor.

* * * * *

UNITED STATES PATENT AND TRADEMARK OFFICE
CERTIFICATE OF CORRECTION

Page 1 of 1

PATENT NO. : 10,957,433 B2
APPLICATION NO. : 16/702510
DATED : March 23, 2021
INVENTOR(S) : Michael Lucas et al.

It is certified that error appears in the above-identified patent and that said Letters Patent is hereby corrected as shown below:

In the Specification

Column 28, Line 24, "MR/EMIR" should be --EHR/EMR--.

Column 28, Line 32, "EMIR/MR" should be --EMR/EHR--.

Column 39, Line 25, "EMIR/MR" should be --EMR/EHR--.

In the Claims

Column 56, Lines 63-64, Claim 2, "category categories" should be --categories--.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*